US012619939B2

(12) United States Patent
Prywes et al.

(10) Patent No.: US 12,619,939 B2
(45) Date of Patent: May 5, 2026

(54) SYSTEMS AND METHODS FOR DETERMINING UNNECESSARY INTERNAL SYSTEM UTILIZATION BASED ON PROTOCOL ADHERENCE

(71) Applicant: Optum, Inc., Minnetonka, MN (US)

(72) Inventors: Samara B. Prywes, Burlington, VT (US); James M. Dolstad, Leavenworth, WA (US); Ian M. Smith, Chanhassan, MN (US); Salina Yip, San Gabriel, CA (US); Maxine Goldsmith, West Hartford, CT (US); Rajiv Arya, Skillman, NJ (US); Yao Zhang, La Canada Flintridge, CA (US)

(73) Assignee: Optum, Inc., Minnetonka, MN (US)

( * ) Notice: Subject to any disclaimer, the term of this patent is extended or adjusted under 35 U.S.C. 154(b) by 17 days.

(21) Appl. No.: 18/400,084

(22) Filed: Dec. 29, 2023

(65) Prior Publication Data

US 2025/0217749 A1     Jul. 3, 2025

(51) Int. Cl.
 *G06Q 10/0639* (2023.01)
 *G06Q 10/0635* (2023.01)
 *G16H 20/10* (2018.01)

(52) U.S. Cl.
 CPC ..... *G06Q 10/0639* (2013.01); *G06Q 10/0635* (2013.01); *G16H 20/10* (2018.01)

(58) Field of Classification Search
 CPC . G06Q 10/0639; G06Q 10/0635; G16H 20/10
 See application file for complete search history.

(56) References Cited

U.S. PATENT DOCUMENTS

| | | | |
|---|---|---|---|
| 8,428,963 B2 | 4/2013 | Underwood et al. | |
| 9,946,840 B1 | 4/2018 | Kemp | |
| 10,356,577 B1 * | 7/2019 | Kugler ................. | H04W 4/029 |
| 10,665,334 B2 | 5/2020 | Baniameri et al. | |
| 10,915,605 B2 | 2/2021 | Stadler et al. | |
| 2005/0091083 A1 * | 4/2005 | McGuigan .............. | G16Z 99/00 |
| | | | 705/3 |
| 2016/0266930 A1 * | 9/2016 | Jones ............... | G06Q 10/06311 |
| 2018/0181712 A1 | 6/2018 | Ensey et al. | |
| 2019/0027238 A1 | 1/2019 | Hanina et al. | |

(Continued)

OTHER PUBLICATIONS

Corinne M. Hohl, Prospective Validation of Clinical Criteria to Identify Emergency Department Patients at High Risk for Adverse Drug Events, 2018, p. 1016-1019 (Year: 2018).*

*Primary Examiner* — Ibrahim N El-Bathy
(74) *Attorney, Agent, or Firm* — Bookoff McAndrews, PLLC

(57) ABSTRACT

Systems and methods are disclosed for determining unnecessary internal system utilization based on protocol adherence. A method includes receiving a first data object, generating an entity data object, and generating a verified entity data object based on comparing one or more metrics of the entity data object against one or more predetermined threshold values, wherein entities of the verified entity data object are a subset of the entities of the entity data object. The method further includes generating a compliance indicator for each entity of the verified entity data object. The method furthermore includes generating a utilization adjustment data object and causing the utilization adjustment data object to be displayed on a Graphical User Interface (GUI).

19 Claims, 5 Drawing Sheets

(56)                    References Cited

U.S. PATENT DOCUMENTS

| | | | |
|---|---|---|---|
| 2021/0035679 A1 | 2/2021 | Pankoke et al. | |
| 2022/0261712 A1* | 8/2022 | Stone | G06N 20/00 |
| 2023/0044000 A1 | 2/2023 | Ramakrishnan et al. | |
| 2023/0073776 A1* | 3/2023 | Muse | G16H 40/40 |
| 2023/0297936 A1* | 9/2023 | Paul | G06Q 10/0833 |
| | | | 705/333 |

* cited by examiner

HEALTHCARE MANAGEMENT MODULE ⌐126
HEALTHCARE MANAGEMENT MODEL ⌐127

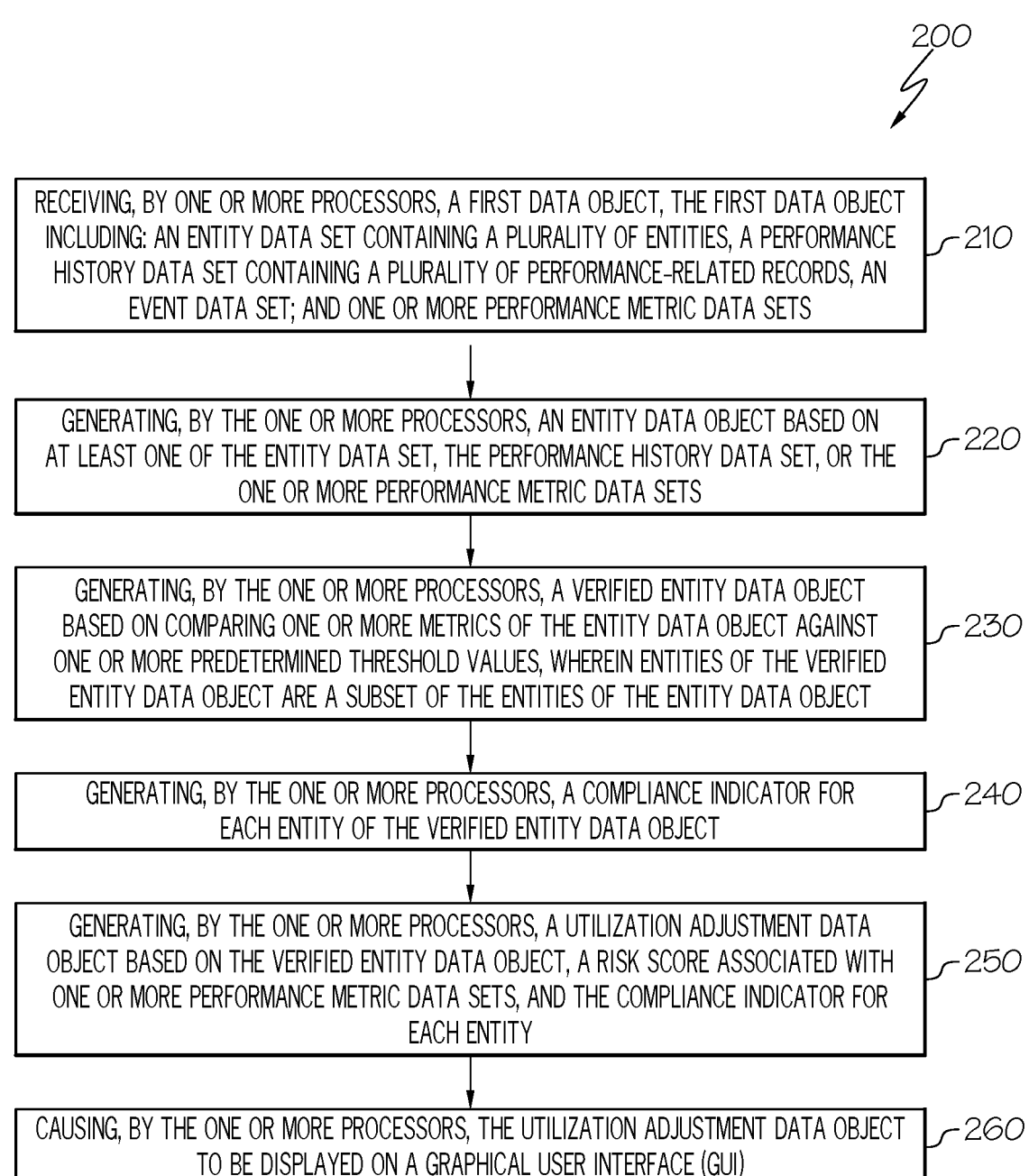

200

RECEIVING, BY ONE OR MORE PROCESSORS, A FIRST DATA OBJECT, THE FIRST DATA OBJECT INCLUDING: AN ENTITY DATA SET CONTAINING A PLURALITY OF ENTITIES, A PERFORMANCE HISTORY DATA SET CONTAINING A PLURALITY OF PERFORMANCE-RELATED RECORDS, AN EVENT DATA SET; AND ONE OR MORE PERFORMANCE METRIC DATA SETS ⌐210

GENERATING, BY THE ONE OR MORE PROCESSORS, AN ENTITY DATA OBJECT BASED ON AT LEAST ONE OF THE ENTITY DATA SET, THE PERFORMANCE HISTORY DATA SET, OR THE ONE OR MORE PERFORMANCE METRIC DATA SETS ⌐220

GENERATING, BY THE ONE OR MORE PROCESSORS, A VERIFIED ENTITY DATA OBJECT BASED ON COMPARING ONE OR MORE METRICS OF THE ENTITY DATA OBJECT AGAINST ONE OR MORE PREDETERMINED THRESHOLD VALUES, WHEREIN ENTITIES OF THE VERIFIED ENTITY DATA OBJECT ARE A SUBSET OF THE ENTITIES OF THE ENTITY DATA OBJECT ⌐230

GENERATING, BY THE ONE OR MORE PROCESSORS, A COMPLIANCE INDICATOR FOR EACH ENTITY OF THE VERIFIED ENTITY DATA OBJECT ⌐240

GENERATING, BY THE ONE OR MORE PROCESSORS, A UTILIZATION ADJUSTMENT DATA OBJECT BASED ON THE VERIFIED ENTITY DATA OBJECT, A RISK SCORE ASSOCIATED WITH ONE OR MORE PERFORMANCE METRIC DATA SETS, AND THE COMPLIANCE INDICATOR FOR EACH ENTITY ⌐250

CAUSING, BY THE ONE OR MORE PROCESSORS, THE UTILIZATION ADJUSTMENT DATA OBJECT TO BE DISPLAYED ON A GRAPHICAL USER INTERFACE (GUI) ⌐260

FIG. 2

SYSTEMS AND METHODS FOR DETERMINING UNNECESSARY INTERNAL SYSTEM UTILIZATION BASED ON PROTOCOL ADHERENCE

TECHNICAL FIELD

The present disclosure generally relates to the field of data analytics. In particular, the present disclosure relates to systems and methods for modeling protocol complexity based on analyzing various data sources and predicting the level of protocol adherence to generate interventions for increased resource utilization efficiency.

BACKGROUND

Ambulatory Care Sensitive Conditions (ACSCs) are conditions that can be effectively managed in external settings, preventing the need for internal system utilization. Adherence to recommended protocols such as, e.g., medication regimen, is a crucial element in the successful management of these conditions. However, complex protocols can present a significant barrier to optimal adherence. Existing strategies to manage this issue include protocol reconciliation, entity education, reminder systems, and simplification of protocols whenever possible. However, these techniques suffer from one or more issues and may be improved in one or more ways.

For instance, current techniques often struggle to identify and respond to the individual factors that contribute to an entity's ability to adhere to a complex protocol. Protocol reconciliation is a useful tool, but it primarily focuses on ensuring correct prescription and usage, rather than simplifying the protocol itself. Entity education initiatives are crucial, yet they may not fully address the challenges posed by complex protocols, nor are they sufficiently personalized. Reminder systems can be beneficial but rely heavily on entity engagement and technological capabilities. The process of simplifying protocols is often reactive, rather than proactive, and may not adequately consider the entity's unique circumstances and capabilities. The consequence of these shortcomings includes suboptimal protocol adherence, which can lead to poorer management of entity's conditions and increased internal system and/or emergency resource utilization.

Therefore, there is a need for a more sophisticated and predictive approach to managing protocol adherence in the context of, for example, ACSC management.

This disclosure is directed to addressing the above-mentioned challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

The present disclosure addresses the technical problem(s) described above or elsewhere in the present disclosure and improves the state of conventional healthcare management techniques.

In some aspects, the techniques described herein relate to a computer-implemented method including: receiving, by one or more processors, a first data object, the first data object including: an entity data set containing a plurality of entities; a performance history data set containing a plurality of performance-related records; an event data set; and one or more performance metric data sets; generating, by the one or more processors, an entity data object based on at least one of the entity data set, the performance history data set, or the one or more performance metric data sets; generating, by the one or more processors, a verified entity data object based on comparing one or more metrics of the entity data object against one or more predetermined threshold values, wherein entities of the verified entity data object are a subset of the entities of the entity data object; generating, by the one or more processors, a compliance indicator for each entity of the verified entity data object; generating, by the one or more processors, a utilization adjustment data object based on the verified entity data object, a risk score associated with one or more performance metric data sets, and the compliance indicator for each entity; and causing, by the one or more processors, the utilization adjustment data object to be displayed on a Graphical User Interface (GUI).

In some aspects, the techniques described herein relate to a system including memory and one or more processors communicatively coupled to the memory, the one or more processors configured to: receive a first data object, the first data object including: an entity data set containing a plurality of entities; a performance history data set containing a plurality of performance-related records; an event data set; and one or more performance metric data sets; generate an entity data object based on at least one of the entity data set, the performance history data set, or the one or more performance metric data sets; generate a verified entity data object based on comparing one or more metrics of the entity data object against one or more predetermined threshold values, wherein entities of the verified entity data object are a subset of the entities of the entity data object; generate a compliance indicator for each entity of the verified entity data object; generate a utilization adjustment data object based on the verified entity data object, a risk score associated with one or more performance metric data sets, and the compliance indicator for each entity; and cause the utilization adjustment data object to be displayed on a Graphical User Interface (GUI).

In some aspects, the techniques described herein relate to one or more non-transitory computer-readable storage media including instructions that, when executed by one or more processors, cause the one or more processors to: receive a first data object, the first data object including: an entity data set containing a plurality of entities; a performance history data set containing a plurality of performance-related records; an event data set; and one or more performance metric data sets; generate an entity data object based on at least one of the entity data set, the performance history data set, or the one or more performance metric data sets; generate a verified entity data object based on comparing one or more metrics of the entity data object against one or more predetermined threshold values, wherein entities of the verified entity data object are a subset of the entities of the entity data object; generate a compliance indicator for each entity of the verified entity data object; generate a utilization adjustment data object based on the verified entity data object, a risk score associated with one or more performance metric data sets, and the compliance indicator for each entity; and cause the utilization adjustment data object to be displayed on a Graphical User Interface (GUI).

It is to be understood that both the foregoing general description and the following detailed description are example and explanatory only and are not restrictive of the detailed embodiments, as claimed.

BRIEF DESCRIPTION OF THE DRAWINGS

The accompanying drawings, which are incorporated in and constitute a part of this specification, illustrate various example embodiments and together with the description, serve to explain the principles of the disclosed embodiments.

FIG. 2 is a flowchart showing a method for determining unnecessary internal system utilization based on protocol adherence, according to some embodiments of the disclosure.

DETAILED DESCRIPTION

Figure 1A:
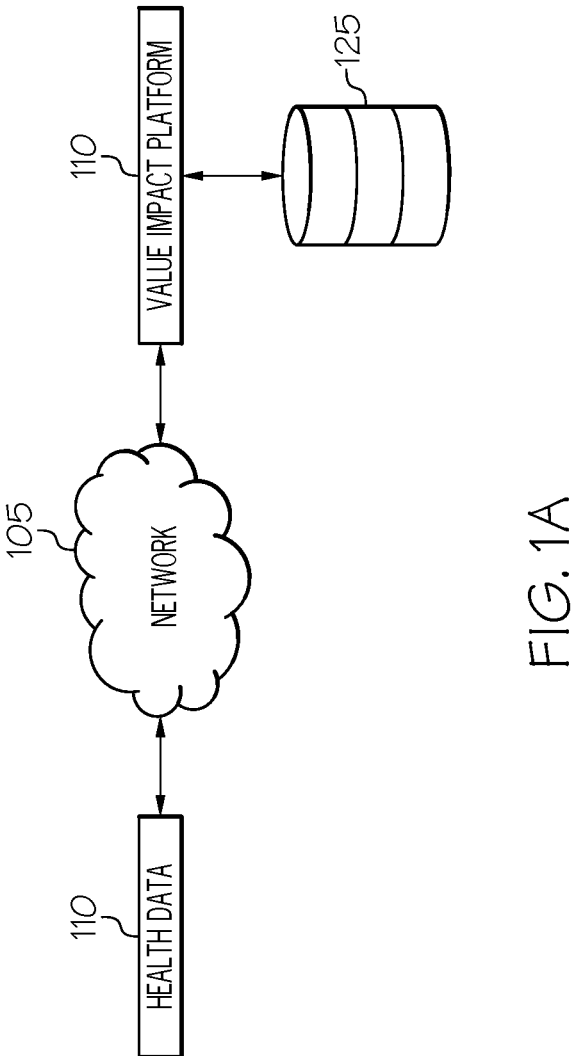
FIG. 1A is a diagram showing an example of a system configured for healthcare management, according to some embodiments of the disclosure.

The present disclosure relates to the field of data analytics and artificial intelligence. Various embodiments of this disclosure relate generally to techniques for predicting unnecessary internal system resource utilization, and, more particularly, to systems and methods for modeling predicted unnecessary internal system resource utilization and interventions to increase efficiency of resource utilization.

As previously discussed, current methods for managing Ambulatory Care Sensitive Conditions often fall short in delivering personalized entity management, addressing communication lapses, ensuring consistent adherence to external follow-ups, and utilizing accurate predictive models to capture the intricate nature of ACSC risk.

To address these concerns, a centralized system and method are provided which facilitate the comprehensive monitoring, analysis, and optimization of program/protocol adherence related to entity management and interventions. This system adeptly integrates multiple data sets, combining various attributes, events, and performance metrics of the entities. By employing advanced analytical methodologies, such as machine-learning algorithms, the system is adept at identifying patterns and correlations that suggest inefficient and/or unnecessary internal system resource allocation or utilization and/or risks associated with non-adherence of medication protocols based on regimen complexity. Furthermore, these analyses not only provide insights but also actionable recommendations to improve the adherence to one or more protocols and reduce complexity. Moreover, the systems and methods described herein leverage data that is unique to individual entities and addresses potential entity interventions at the entity-level. The system and method further include monitoring of the entity data and its changes over time, adjusting, updating, and retraining the applied models to account for changes in entity data, resulting in higher adoption of interventions, improved care pathways for the entities, and reduced complexity of medication protocols. The above technical improvements, and additional technical improvements, will be described in detail throughout the present disclosure. Also, it should be apparent to a person of ordinary skill in the art that the technical improvements of the embodiments provided by the present disclosure are not limited to those explicitly discussed herein, and that additional technical improvements exist.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the disclosure is not to be considered as limited by the foregoing description.

Various non-limiting embodiments of the present disclosure will now be described to provide an overall understanding of the principles of the structure, function, and use of systems and methods disclosed herein for healthcare management outcomes.

Reference to any particular activity is provided in this disclosure only for convenience and not intended to limit the disclosure. A person of ordinary skill in the art would recognize that the concepts underlying the disclosed devices and methods may be utilized in any suitable activity. For example, while the present disclosure is in the context of healthcare management, one of ordinary skill would understand the applicability of the described systems and methods to similar tasks in a variety of context or environments. The disclosure may be understood with reference to the following description and the appended drawings, wherein like elements are referred to with the same reference numerals.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

It will also be understood that, although the terms first, second, third, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

As used herein, a "machine-learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine-learning model is generally trained using training data, e.g., experiential data and/or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration.

Training the machine-learning model may include one or more machine-learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc. After training the machine-learning mode, the machine-learning model may be deployed in a computer application for use on new input data that it has not been trained on previously.

FIG. 1A is a diagram showing an example of a system that is capable of healthcare management, according to some embodiments of the disclosure. The depicted network environment, designated as 100, is in accordance with a specific embodiment of the current disclosure. The network environment 100 encompasses a communication infrastructure, such as network 105, which is accompanied by health data 110, and is further equipped with a value impact platform 120 integrated with a database 125.

In one embodiment, various components of the network environment 100 interact with each other through the network 105. The network 105 facilitates communication between the value impact platform 120 and one or more other systems, including one or more data sets, such as (but not limited to) health data 110. The one or more data sets and/or health data 110 includes data, one or more data entries and/or data objects associated with or comprising medical records. The network 105 includes one or more networks such as a data network, a wireless network, a telephony network, or any combination thereof.

The health data 110 encompasses an array of structured and unstructured information pertaining to the health of individuals. The health data, in some embodiments, is in the form of one or more data object, and encompass various facets, including but not limited to, health plan-provider contracts, member files, provider records, PCP to member attribution, medical and pharmacy claims, as well as insights from impact analytics, geographical and context based pricing indexes, Social Determinants of Health (SDoH), NYU Avoidable Preventable classification, Admit, Discharge, Transfers (ADT), Area Deprivation Index (ADI), Rural Urban (RUCA), risk and quality analytics, and the like. This diverse health data repository, comprising details such as demographic data, medical histories, insurance claims, and other health metrics, finds its repository in storage, which may take the form of local or remote data storage solutions, including file servers and cloud-based storage systems, among others.

The database 125 is used to support the storage and retrieval of data related to one or more data sets and/or data objects, such as the health data 110, storing metadata and/or healthcare data about one or more population represented in the health data 110, as well as any information received from the value impact platform 120. The database 125 can consist of one or more systems, such as a relational database management system (RDBMS), a NoSQL database, a graph database, or the like, depending on the requirements and use cases of the network environment 100.

In one embodiment, the database 125 is any type of database, such as relational, hierarchical, object-oriented, etc., wherein data is organized in tables, lookup tables, or other suitable manners. The database 125 stores and provides access to data utilized by the value impact platform 120. The database 125 stores information related to the health data 110 as well as information generated by the value impact platform 120. The database 125 can store various types of information to aid in the healthcare management.

In one embodiment, the database 125 includes a machine learning-based training database that maps relationships, associations, connections, or the like between input parameters from the health data 110 and output parameters representing the one or more metrics for management of healthcare. For example, the training database can include machine learning algorithms that learn mappings between medical data inputs and one or more of utilization, adherence, sensitive condition treatment outputs, or the like. The training database can be routinely updated based on additional machine learning.

The value impact platform 120 communicates with other components of the network 105 using known or developing protocols. These protocols govern interactions between network nodes and define rules for generating, receiving, and interpreting information sent over communication links. The protocols operate at different layers, from generating physical signals to identifying software applications sending or receiving the information.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers.

In operation, the network environment 100 provides a framework for analyzing large amounts of health data 110, leveraging data analytics, artificial intelligence, and database technologies to support various use cases and applications. For example, the network environment 100 can be used to generate metrics, data objects, and insights from one or more data sets, such as the health data 110, based on user-defined criteria or a plurality of parameters.

To perform these tasks, the value impact platform 120 utilizes techniques such as the healthcare management model 127 (FIG. 1C), which analyzes the population data 110 and identifies one or more healthcare management metrics, which in some embodiments match one or more specified criteria or user input. The value impact platform 120 can also utilize the data collection module 122 and data processing module 124 (FIG. 1B) to gather and prepare the health data 110.

To support storage and retrieval of data related to the healthcare management metrics, the database 125 stores metadata about the health data 110, such as data sources, types, and formats. The database 125 also stores information about the health management metrics output by the value impact platform 120, such as health criteria, identifiers, and statistics.

In addition to healthcare management, the network environment 100 can support other applications like data visualization, search, and predictive modeling. For example, the network environment 100 could allow users using user devices to search the health data 110 for one or more metrics matching certain criteria, or visualize healthcare metric statistics through interactive graphs and charts.

Figures 1B, 1C:
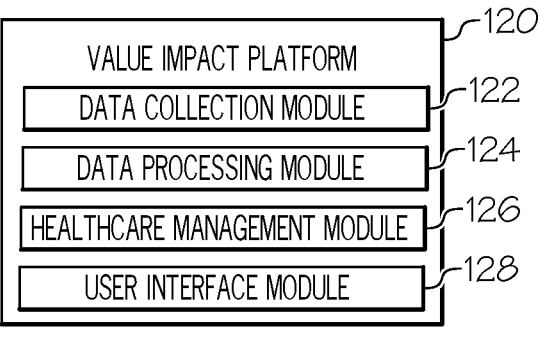
FIG. 1B is a diagram of example components of a value impact platform, according to some embodiments of the disclosure.
FIG. 1C is a diagram of example components of a healthcare management module, according to some embodiments of the disclosure.

FIG. 1B is a diagram of example components of a value impact platform 120, according to some embodiments of the disclosure. Referring to FIG. 1B, the value impact platform 120 is a component of the network environment 100. The value impact platform 120 provides the capabilities to analyze one or more data sets, such as health data 110 and generate one or more data object including one or more healthcare management metric. As used herein, terms like "component" or "module" encompass hardware and/or software implemented by a processor or the like. For example, the value impact platform 120 includes components for collecting, processing, and analyzing health data as well as generating one or more data object including one or more healthcare management metrics. To that end, the value impact platform 120 includes modules such as a data collection module 122, a data processing module 124, a healthcare management module 126, and a user interface module 128. It is contemplated that the functions of these modules could be combined into fewer modules or performed by other modules with equivalent functionality.

In some embodiments, the data collection module 122 of the value impact platform 120 undertakes the collection of data from one or more data sets, such as health data 110, during the operation of the environment 100. The data collection module 122 is equipped to receive a myriad of data types such as, but not limited to, health plan provider contract data, provider data, member data including member eligibility data, PCP-to-member attribution data, medical and pharmacy claims data, proprietary or generated data, such as impact analytics data, pricing data, risk and quality analytics data, or the like, Healthcare Effectiveness Data and Information Set (HEDIS) quality metrics data, clinical prediction analytics, financial savings factors, Social Determinants of Health (SDoH) data, NYU Avoidable Preventable classification data, Area Deprivation Index (ADI) data, Admit, Discharge, and Transfer (ADT) data, Rural-urban Commuting Area (RUCA) data, proprietary episode treatment groupers (ETGs) data, proprietary service categories data, AHRQ groupers data, member geographic data, Drug Class Codes (DCCs), and the like.

In some embodiments, the health plan provider contract data includes, but is not limited to, the identification and credentials of providers, specifics of the health plans offered, a compilation of service and billing codes, agreed reimbursement rates, payment terms, the scope of benefit coverage, eligibility prerequisites for patients, protocols for authorizations and referrals, quality and performance benchmarks, procedures for dispute resolution, duration and termination information, privacy and confidentiality terms, regulatory adherence protocols, amendment procedures for the contract, utilization review guidelines, potential risk-sharing agreements, credentialing processes for healthcare providers, specifications regarding pharmacy formularies, and the like.

In some embodiments, the provider data includes, but is not limited to, identifiers such as names, addresses, contact details, specialties, qualifications, and tax identification numbers associated with providers. The data set also includes credentialing information, which verifies the qualifications and backgrounds of the providers, their affiliations with hospitals or other medical institutions, the insurance plans they accept, and their availability for patient appointments. In addition, the provider data contains historical data on the types and volumes of procedures performed, quality of care metrics, patient outcomes, and satisfaction scores, as well as data on billing practices and reimbursement rates.

In some embodiments, the member data includes, but is not limited to, identifiers such as names, birth dates, and member identification numbers associated with members. The member data further contains demographic details like addresses, contact information, gender, and employment information if relevant to the health plan. The health-related aspects of the data set cover a member's entire medical history with the plan, including plan enrollment dates, coverage details, dependents, benefit utilization records, and claims history. Additionally, the member data includes members' health conditions, diagnoses, treatment histories, and outcomes.

In some embodiments, the PCP-to-member attribution data includes, but is not limited to, one or more mappings between primary care providers (PCPs) and their attributed members, thereby identifying and/or linking individuals enrolled in a health plan and their designated primary caregivers. The PCP-to-member attribution includes data related to member identification numbers, names, and demographic information, alongside corresponding identifiers and credentials of the attributed PCPs. The PCP-to-member attribution data includes the duration of the member-PCP relationship, visit histories, and the nature of primary care services rendered. Additionally, in some embodiments, the PCP-to-member attribution includes data on care continuity, referral patterns, and the effectiveness of the PCP in managing the member's health, including preventative care and chronic disease management.

In some embodiments, medical and pharmacy claims data includes, but is not limited to, comprehensive records of members' interactions with healthcare systems, reflecting services rendered and pharmaceuticals provided. This includes data on claims submissions, detailing dates of service, types of services, service providers, claim amounts, and payment outcomes. Each entry correlates with member identification numbers and the associated healthcare providers or pharmacies. The medical and pharmacy claims also includes diagnostic codes, procedure codes, and pharmacy billing information, providing insights into the medical conditions treated and the medications dispensed. Furthermore, in some embodiments, the medical and pharmacy claims data includes a historical overview of members' claims over time, which can be analyzed to ascertain patterns in healthcare utilization, medication adherence, and the overall efficiency of healthcare services delivered.

In some embodiments, impact analytics data, such as data generated from a proprietary analytics engine, includes but is not limited to, one or more data sets which provide insights and/or data related to healthcare efficiency, costs, and outcomes. The impact analytics data aggregates and analyzes various aspects of healthcare services, encompassing medical claims, pharmacy claims, clinical data, and program participation records. The impact analytics data includes metrics on healthcare utilization, financial performance, clinical outcomes, and patient adherence to treatment regimens. Additionally, in some embodiments, this impact analytics data encompasses predictive analytics on risk stratification, care gaps, and potential interventions. The data set also integrates benchmarking against normative data or best practices, thereby enabling healthcare providers and payers to measure the effectiveness of their services against established standards.

In some embodiments, pricing data, such as data generated from a proprietary pricing engine, includes, but is not limited to, extensive data sets focused on the financial aspects of healthcare services. The pricing data encapsulates information on current market rates for various medical procedures and services, pharmaceutical pricing, and the costs associated with different healthcare providers. The pricing data comprises details on negotiated contract rates, reimbursement models, historical pricing trends, and comparative analysis across different regions or service providers. Additionally, in some embodiments, the pricing data may integrate cost forecasting, budget impact models, and scenario analyses.

In some embodiments, risk and quality analytics data, such as data generated from a proprietary analytics engine, includes but is not limited to, an array of data points that enable evaluation and monitoring of the quality, efficiency, and safety of healthcare delivery that encompasses risk assessments, quality measures, patient safety indicators, and compliance with clinical guidelines. The risk and quality analytics data includes outcomes data, risk adjustment factors, and analytics related to population health management. Additionally, in some embodiments, the risk and quality analytics data includes data related to care management programs, member health assessments, and provider performance evaluations.

In some embodiments, Healthcare Effectiveness Data and Information Set (HEDIS) quality metrics data includes, but is not limited to, one or more standardized performance measures that are used to assess the quality of care and services provided by health plans. The HEDIS quality metrics data includes one or more indicators across various domains of care, including preventive health services, chronic disease management, mental health care, substance use treatment, care coordination, and the like. The HEDIS quality metrics data includes data related to healthcare effectiveness, patient safety, timeliness of care, and patient engagement. Additionally, in some embodiments, the HEDIS quality metric data may also encompass measures of utilization and risk-adjusted health outcomes.

In some embodiments, clinical prediction analytics data includes, but is not limited to, patient demographics, historical clinical data, treatment records, real-time health monitoring data, and the like. The prediction analytics data, in some embodiments, includes data generated by one or more predictive models and algorithms that analyze patterns in the data to anticipate future health events, such as hospital readmissions, disease progression, or the likelihood of specific health conditions developing. Additionally, in some embodiments, the clinical prediction analytics data includes data indicative of risk scores, potential gaps in care, and suggested preventative measures.

In some embodiments, financial savings factors data includes, but is not limited to, data related to cost avoidance, reduction in unnecessary medical procedures, efficiencies gained through improved care coordination, and savings from formulary management in pharmacy benefits. Additionally, in some embodiments, the financial savings factors data includes data on member cost-sharing amounts, provider network contracting savings, and the impact of wellness programs on overall healthcare costs.

In some embodiments, Social Determinants of Health (SDoH) data includes, but is not limited to, data points related to non-medical factors influencing patient health outcomes. The SDoH data encompasses socio-economic status, education level, neighborhood and physical environment, employment status, social support networks, and the like. The SDoH data, in some embodiments, includes information collected through patient surveys, community health assessments, and public health databases. Additionally, in some embodiments, the SDoH data includes indicators of health disparities, access to healthcare services, and environmental risk factors.

In some embodiments, NYU Avoidable Preventable classification data includes, but is not limited to, data related to metrics that categorize healthcare events deemed either avoidable or preventable with proper and timely medical care, patient education, and other interventions. This classification data includes data elements such as emergency department visits that could be managed in primary care settings, hospital admissions for conditions preventable through outpatient services, and incidences of chronic disease complications that can be mitigated through proper management and lifestyle adjustments.

In some embodiments, Area Deprivation Index (ADI) data includes, but is not limited to, data that ranks neighborhoods by socioeconomic status disadvantage in a region or across the nation. The ADI data includes data related to income, education, employment, housing quality, and other socioeconomic factors which demonstrate disparities across different regions. The ADI data, in some embodiments, is arranged by region, such as by zip code.

In some embodiments, Admit, Discharge, and Transfer (ADT) data includes, but is not limited to, operational data detailing patient movement within a healthcare facility or across facilities. This data set includes timestamps and related information for patient admissions, discharges, and transfers among different departments or care settings. The ADT data, in some embodiments, is collected in real-time, facilitating immediate updates to a patient's status and location. Additionally, in some embodiments, the ADT data includes identifiers that can be used to track patient flow, manage bed occupancy, and coordinate care transitions effectively.

In some embodiments, Rural-urban Commuting Area (RUCA) data includes, but is not limited to, data that categorizes regions, such as U.S. census tracts, using measures of population density, urbanization, and daily commuting. The RUCA data, in some embodiments, provides data relating to the rural-urban continuum, distinguishing between areas, such as metro and rural. Additionally, in some embodiments, the RUCA data includes the primary commuting flows to identify the social and economic integration of locales In some embodiments, Drug Class Codes (DCC) data includes numerical and alphabetical identifiers that categorize drugs based on their pharmacological properties, therapeutic effects, chemical structure, and mechanism of action. The DCC data is structured to represent relationships between different drugs and their respective classes, enabling the identification of similar or related compounds. The DCC data is stored in a database where each drug is linked to one or more drug class codes, which in turn are associated with detailed descriptions of the drug class characteristics.

The data is ingested into the system via multiple pathways, thereby providing flexibility in the collection mechanism. Specifically, one pathway includes an Application Programming Interface (API) that establishes a secure communication channel for automated data transfer between the data collection module 122 and external data sources, thus facilitating real-time or batch-based data acquisition. Another pathway allows for manual input by authorized users via a dedicated user interface, where such input can be executed through file uploads or direct data entry into predefined fields. Additionally, data intake can be accomplished through third-party integrations, middleware, or direct database queries that serve to populate the database 125. The data collection module 122 further incorporates data validation and integrity checks to ensure the consistency and reliability of the ingested data. By offering a plurality of data intake methodologies, the data collection module 122 ensures robust and comprehensive data assimilation for downstream processing.

The data processing module 124 of the value impact platform 120 partakes in the processing and preparation of the data for further analysis by the healthcare management module 126. The data processing module 124 engages in the cleaning of the data, removal of irrelevant or redundant information, and conversion of the data into a format suitable for further processing by the healthcare management module 126. The data processing module 124 is configured to augment the initial data collection by transforming the raw, heterogeneous data into a unified, standard format, which is useful for accurate and efficient downstream processing. Specifically, the data processing module 124 executes a series of algorithms responsible for data standardization, thereby reconciling discrepancies in data types, units, or terminologies originating from disparate sources.

The data processing module 124 also integrates error-handling mechanisms to identify and rectify potential data inaccuracies or anomalies. Such mechanisms may involve rule-based checks, probabilistic data matching, or data imputation techniques, all aimed at preserving data quality and integrity. Furthermore, the data processing module 124 may incorporate parallel processing capabilities to concurrently handle multiple data streams, thereby ensuring timely and efficient data throughput. This is particularly advantageous when dealing with large-scale data sets or real-time analytics where swift data processing is desired.

The healthcare management module 126, upon receiving the prepared data from data processing module 124, applies algorithms and models, such as healthcare management model 127, to generate one or more data objects including one or more healthcare management metrics, based on the input data. The healthcare management module 126 utilizes various algorithms and employs a variety of models to accomplish its task. The healthcare management module 126 engages in the computational manipulation of the ingested data. Utilizing the healthcare management model 127 as one among a possible array of analytical frameworks, the healthcare management module 126 applies a combination of algorithmic and machine-learning methodologies to generate one or more healthcare management metrics based on the input data. Such metrics serve as quantifiable representations of various aspects of healthcare management.

In one embodiment, the healthcare management module 126 applies algorithms related to clinical opportunities methodology. This methodology integrates diverse sets of processed data, such as medical claims, financial data, clinical histories, medication protocols, and/or any other data as discussed herein, or the like, to produce a healthcare management metric that reflects opportunities for cost and quality optimization in healthcare delivery.

In another embodiment, the healthcare management module 126 employs machine-learning-based prediction algorithms to produce metrics that predict future healthcare events. These could include patient risk stratification, likelihood of hospital readmission, care treatment pathway offsets, medication adherence risk, or the like. The predictive models, which are a part of the healthcare management model 127, use features extracted from the processed data, such as social determinants of health, historical medical data, area deprivation index scores, one or more other features extracted from the processed data as discussed herein, or a combination thereof.

Additionally, the healthcare management module 126 in some embodiments uses value impact modeling to generate healthcare management metrics that evaluate the resource efficiency (such as economic, staffing, or material usage implications) of distinct clinical interventions or pathways. These metrics are derived from simulations that are conducted using various models, each designed to measure the financial impact of specific healthcare decisions.

The healthcare management module 126, in some embodiments, further produces healthcare management metrics that represent aggregated patient worklists or next-best-action recommendations. These metrics are formulated through a combination of rule-based algorithms and probabilistic models, which evaluate and incorporate qualitative variables like HEDIS quality metrics and medical and pharmacy claims.

After the healthcare management module 126 has generated the one or more data objects including one or more healthcare management metric based on the input data, a user interface generated on a user device via the user interface module 128 displays the results to the user at an appropriate time. The user interface provides an interactive and intuitive interface, enabling the user to view, modify, or confirm the generated results. The user interface also enables the user to provide feedback or additional information to improve the healthcare management process or adjust the healthcare management model 127 accordingly. The user interface module 128 is also configured to receive a user input via an interactive interface, the user input being one or more parameters.

FIG. 1C is a diagram of example components of a healthcare management module 126, according to some embodiments of the disclosure. FIG. 1C provides a more detailed view of the healthcare management module 126 and its relationship with the healthcare management model 127 within the value impact platform 120. As depicted, the healthcare management module 126 includes a healthcare management model 127. The healthcare management model 127 is configured or trained to determine appropriate healthcare management metrics, in the form of one or more data objects, related to resource utilization, care and/or protocol adherence, care outcomes, resource efficiency, and the like, based on various factors, such as those reflected in the health data 110. Furthermore, the healthcare management model 127 also takes into account changes to the health data and/or to the populations within the health data to increase the likelihood of an accurate response.

The healthcare management model 127, as part of the healthcare management module 126, orchestrates the creation of healthcare management metrics, such as data objects, from health data 110. This algorithm is agnostic to its underlying implementations and is designed to accommodate various types of algorithms, either individually or in combination, to achieve the desired outcomes. In some embodiments, the healthcare management metrics generated by the healthcare management model 127 pertain to predicted utilization of resources and services, projected complexity of medication regimens, identified categories associated with risks and/or severities, or other relevant aspects related to patient care and treatment planning. It should be noted that while the described implementation involves a predicative model, alternative configurations incorporate other models or approaches depending upon the specific needs and requirements of the healthcare facility and patients served. For example, the healthcare management model 127, in some embodiments, analyzes historical patterns in healthcare usage data to develop predictions about future trends. This information is then be used to optimize staffing levels, inventory management, equipment maintenance schedules, and other logistical considerations necessary for providing efficient and effective medical care. Additionally, the generated metrics assist clinicians in identifying patients who would benefit from targeted interventions or early discharge planning efforts, thereby reducing hospital stays and improving overall patient health outcomes.

In some embodiments, the value impact platform 120 is configured to support contract ingestion and standardization. The data collection module 122 is configured to receive contract terms among other types of healthcare-related data. Upon collection, these contract terms are forwarded to and received by the data processing module 124. The data processing module transforms the heterogeneous contract data into a unified, structured format that is suitable for subsequent processing by the healthcare management module 126 and storage within the database 125.

The data processing module 124 employs algorithms designed specifically for contract standardization. These algorithms reconcile variances in contract terminologies, units, and conditions, thereby eliminating inconsistencies that could potentially impact the quality of the generated healthcare management metrics. This standardization process results in the normalization or standardization of contracts from disparate sources that can be accurately compared, analyzed, and integrated within the healthcare management framework enabled by the value impact platform 120.

In addition to terminology reconciliation, the data processing module 124 performs the task of structuring the ingested contract data. This involves the breaking down complex contract clauses into constituent elements, which are then mapped to predefined fields within the database 125. By doing so, the data processing module 124 ensures that the contract data is organized in a manner conducive to efficient query execution and data retrieval. Following the completion of the contract ingestion and standardization process, the standardized contract data is stored in the database 125 and is made accessible to the healthcare management module 126 for subsequent analytical operations.

In some embodiments, the data processing module 124 is configured to combine two or more contracts for the purpose of generating healthcare management metrics. The platform identifies contracts with terms sufficiently similar to warrant amalgamation into a single data object. Subsequently, these unified contract data objects are stored in the database 125 and are rendered accessible to the healthcare management module 126 for further analytical activities. The data processing module 124 incorporates rules-based mechanisms or utilizes one or more models or algorithms to establish the suitability of combining specific contracts. In a rules-based approach, pre-defined combination rules are set by one or more users of the system. These rules specify criteria that contract terms must meet to be considered similar, such as identical service categories, payment models, geographical locations, or the like. In some embodiments, the data processing module 124 employs computational models or algorithms to assess the suitability of contracts for combination. These algorithms analyze attributes such as contract duration, parties involved, and other contractual elements, and apply statistical or machine-learning techniques to make determinations on whether contracts can be combined together.

Once contracts are combined into single data objects, the user, through the user interface module 128, is enabled to select these combinations for analysis. The healthcare management module 126 then generates one or more healthcare management metrics or reports based on the combined contract data objects. The system is further designed to allow the user to modify the selection of combined contracts. Upon such re-selection, the healthcare management module 126 automatically re-generates the healthcare management metrics or reports to reflect the updated corpus of selected contracts.

In some embodiments, the value impact platform 120 generates one or more performance reports for the individual or combined contracts. This performance reporting is formulated based on a combination of input data and the standardized or amalgamated contract data objects stored in the database 125.

In one embodiment, the healthcare management module 126 employs algorithms related to financial performance reports. These algorithms integrate the standardized contract data with other forms of healthcare data, such as medical and pharmacy claims, one or more quality metrics such as HEDIS quality metrics, clinical prediction analytics, or the like, to yield a performance report that assesses the financial implications of the individual or combined contracts. The report covers aspects such as cost-efficiency, quality of care, and adherence to contract terms, among other criteria.

In another embodiment, the healthcare management module 126 uses the clinical opportunity identification methodology to generate performance reports. This methodology combines one or more of the contract data, whether individual or combined, clinical histories, social determinants of health, or other relevant healthcare data to identify opportunities for clinical improvements and cost savings. The resulting performance report provides a granular analysis of the efficacy and efficiency of healthcare service delivery.

For contracts that have been combined, the healthcare management module 126 is configured to generate a unified performance report that represents the aggregated impact of the bundled and/or combined contracts. This unified report comprises metrics such as overall quality improvement and combined compliance rates, synthesized from the individual contracts included in the combination.

Further, in some embodiments, the system enables the user, through the user interface module 128, to interact with the generated reports. Users can select different combinations of contracts, prompting the healthcare management module 126 to re-calculate and re-generate performance reports and/or one or more data object based on the newly selected combinations. This adaptability ensures that users obtain tailored insights that cater to different analytical needs.

In some embodiments, the healthcare management module 126 is configured to perform tasks related to clinical and quality modeling. The module receives input data and standardized or combined contract data from the database 125 and applies a series of algorithms and models for the generation of clinical and quality metrics. These metrics pertain to the assessment of healthcare services, patient outcomes, and compliance with established healthcare standards. The healthcare management module 126 incorporates specific algorithms designated for evaluating quality metrics such as HEDIS scores, patient satisfaction rates, and clinical effectiveness measures. These algorithms integrate with the contract data to discern how specific contractual terms and conditions influence quality outcomes. For example, an algorithm assesses how a payment model specified in a contract impacts the healthcare provider's adherence to HEDIS standards. Similarly, the module includes clinical modeling capabilities that employ advanced algorithms, retrospective models, or machine-learning models. These clinical models incorporate multiple variables from the input data, including but not limited to medical and pharmacy claims, member eligibility, and social determinants of health, to produce actionable insights. For instance, the module utilizes an algorithm that integrates patient medical histories and contract-specific guidelines on pharmaceutical usage to determine optimal drug regimens for individual patients. Moreover, the clinical and quality metrics generated can be included as part of broader performance reports. These reports are displayed through the user interface module 128, which allows users to interact with and interpret the metrics, thereby enabling more informed healthcare management decisions.

In instances where combined contracts are used, the healthcare management module 126 is further configured to generate clinical and quality models that reflect the aggregate effect of these combined contracts. For instance, a unified quality model might be generated that blends the quality metrics from multiple contracts to offer a holistic view of healthcare service quality across an entire healthcare network.

In some embodiments, the healthcare management module 126 incorporates functionalities designed for dynamic scenario modeling. Specifically, the module enables the modeling of scenarios that simulate the impact of various improvement opportunities on performance metrics, particularly with respect to financial, clinical, and quality dimensions. This capability allows users to forecast the outcomes of potential actions or interventions within the healthcare system. For instance, the dynamic scenario modeling employs a modeler which is configured to capture the top n common payer scenarios. This modeler assimilates information from diverse data sources such as financial models, clinical histories, and quality metrics, all of which are stored in the database 125. The modeler then utilizes these data points in conjunction with the contract data, whether individual or combined, to generate a set of scenario options.

Understanding that medical groups often operate under resource constraints, the dynamic scenario Modeler allows the user to selectively focus efforts on one or two key metrics with the objective of optimizing performance against contractual targets. Users interact with this feature via the user interface module 128, where they can specify the level of resource allocation they wish to devote to particular opportunities for improvement. For example, in some embodiments, a user might elect to focus on optimizing HEDIS quality metrics. The dynamic scenario modeler would then simulate the impact of such an optimization on financial performance, considering parameters such as reimbursement rates stipulated in the contract or contracts. Simultaneously, the dynamic scenario modeler would also forecast the implications on clinical performance metrics, such as patient health outcomes or admission rates. By way of another example, in some embodiments, the user could decide to emphasize efforts on cost-saving measures in pharmaceutical spending. Here, the dynamic scenario modeler generates a scenario illustrating how such an effort would affect not just financial metrics like overall spending, but also quality metrics like patient satisfaction and clinical efficacy. In cases involving combined contracts, the dynamic scenario modeler is further configured to aggregate the impacts across the multiple contracts, providing a consolidated view of how resource allocation in selected areas would influence performance metrics at a holistic level.

FIG. 2 is a flowchart showing a method 200 for determining unnecessary internal system utilization. In step 210 the value impact platform 120 receives a first data object. The first data object may comprise one data object or a plurality of data objects, that includes a collection of data sets. In some embodiments, the first data object includes an entity data set containing a plurality of entities. The entity data set encompasses data about one or more members, with each member potentially being associated with one or more providers, such as a healthcare provider.

In some embodiments, the first data object includes a performance history data set and/or data array. The performance history data set includes one or more performance-related metrics, records. In some embodiments, the performance-related records include information about one or more medical claims and/or pharmacy claims associated with one or more entities. In some embodiments, the performance history data set includes information related to medication regimens associated with one or more members. Each medication regimen comprises a plurality of data points indicative of various aspects of medication administration and compliance. For instance, the data set includes, for each medication in the regimen, the specific identification of the medication such as name, generic alternative identifications, dosage form, and manufacturer details (e.g., name, location, or the like).

The performance history data set further includes administration details regarding the medication. Such details encompass prescribed dosage, frequency of administration, route of administration (e.g., oral, intravenous, or the like), and timing or scheduling of doses. Additionally, the performance history data set includes information relating to the duration for which each medication is prescribed, including start and end dates or continuation conditions based on patient response or other criteria.

Also included in the performance history data set are compliance metrics associated with each member's adherence to the prescribed medication regimen. These metrics include, but are not limited to, records of medication taken, timing of each taken medication relative to its prescribed schedule, missed doses, and partial doses (e.g., instances where a portion of a prescribed dose is taken).

The performance history data set also encompasses information regarding the effectiveness and outcomes associated with the medication regimen. Such information comprises data relating to symptom alleviation, side effects experienced, adverse reactions, or interaction effects with other medications or substances. The information relating to effectiveness and outcomes could be derived from various sources including self-reports from members, clinician observations, laboratory test results, or the like.

In addition, the performance history data set incorporates external factors that could influence the effectiveness or adherence to the medication regimen. These factors include lifestyle considerations such as diet, exercise, sleep patterns, substance use (e.g., alcohol, nicotine, or the like), and environmental or contextual factors such as stress levels, occupational factors, seasonal variations, or the like.

In some embodiments, the first data object includes an event data set. The event data set includes one or more data sets and/or arrays, such as such as an episode treatment groupers (ETGs) array, episode risk groupers (ERGs) array, or the like. In some embodiments, ETGs are a classification system used in healthcare to group clinically similar medical events. The ETGs array includes information which is utilized and applied to medical events, such as medical claims data, to aggregate individual, patient-specific medical claims and encounter data into clinically meaningful and discrete units, known as "episodes of care." Each episode represents a distinct phase of a patient's medical treatment, from initial diagnosis through the course of treatment for a particular condition. In some embodiments, the groupers are associated with and/or utilized to identify one or more chronic conditions, such as asthma, CHF, COPD, diabetes, hypertension, or the like.

In some embodiments, ERGs (Episode Risk Groupers) are tools utilized to evaluate and categorize the risk associated with various episodes of care within the healthcare landscape. The ERGs array comprises a multitude of data elements and parameters that collectively contribute to a comprehensive risk assessment of medical events or episodes. Such data elements encompass diagnostic information, procedural details, demographic characteristics of the patient, comorbidities, and historical medical data pertinent to the evaluation of the risk profile of each episode of care. Diagnostic information within the ERGs array includes, but is not limited to, the identification of primary and secondary diagnoses, the specificity of diagnostic codes, and the chronology of diagnoses in relation to each episode of care. Procedural details encapsulated within the ERGs array involve the identification of medical procedures performed, the sequencing of procedures, and the contextual relevance of each procedure within the episode of care. Demographic characteristics embedded within the ERGs array pertain to patient-specific attributes such as age, gender, geographical location, socioeconomic status, or the like. These characteristics are useful in tailoring the risk assessment to the profile of each patient, enabling a more nuanced and individualized evaluation of risk. Comorbidities and historical medical data included in the ERGs array comprise information regarding pre-existing medical conditions, prior medical events, and historical trajectories of medical treatments and outcomes.

In some embodiments, the first data object includes one or more performance metric data sets. In some embodiments, the these performance metrics include additional health data, consisting of a provider data set which relates to one or more providers, insurers, hospital service locations, or the like. In some embodiments, the performance metric data sets include additional information regarding medical claims and medication utilization, such as drug class codes (DCCs). In some embodiments, a drug class codes data set is structured hierarchically to facilitate a systematic classification and organization of pharmaceutical agents. For example, in some embodiments the drug class data set categorizes drugs based on therapeutic class, pharmacological class, and specific chemical entities, among other categories. Each therapeutic class groups drugs according to their primary therapeutic use, while pharmacological classifications delve deeper, focusing on pharmacologic mechanisms. Further granularity is achieved, in some embodiments, through the identification of specific chemical entities or active ingredients, promoting a nuanced understanding of each drug's composition. Augmenting these classifications, the drug class code data set includes metadata, encompassing attributes such as generic and brand names, dosage forms, indications, and contra-indications, and the like. In some embodiments, the performance metric data sets can also include data that is not covered by the entity data set, performance history data set, and event data set, and that were otherwise discussed elsewhere in the present disclosure.

In some embodiments, at step 220 the value impact platform 120 generates an entity data object based on at least one of the entity data set, the performance history data set, or the one or more performance metric data sets. In some embodiments, the entity data object represents a cohesive assembly of information pertinent to each individual entity, where each entity corresponds to a subject or patient within health data 110 and/or the network environment 100.

The generation of the entity data object involves various computational processes aimed at consolidating, organizing, and/or refining the data associated with and/or contained in the entity data set, performance history data set, and the performance metric data sets. As discussed, the entity data set encompasses a multitude of entities, each entity being associated with an array of attributes and historical data that are useful in the subsequent analysis and evaluations.

In some embodiments, the method includes one or more data combinations and manipulations of the consolidated data within the entity data object. For instance, data from the entity data set could be interlinked with corresponding data from the performance history data set and performance metric data sets, facilitating a comprehensive, multi-dimensional view of each entity's historical and current status, behaviors, and performances within the healthcare environment.

For each entity within the entity data object, the value impact platform 120, or one or more aspects of the value impact platform 120, performs one or more data manipulations and/or generations. In some embodiments, a processor applies data associated with one or more episode treatment groupers (ETGs) to the medical and pharmacy claims, enabling a structured categorization and grouping of the claims data, thereby facilitating a more organized and efficient data processing and analysis.

In some embodiments, the data associated with the episode treatment groupers function as algorithmic tools, applying a systematic logic to classify and group medical and pharmacy claims into coherent episodes of care (e.g., classify the claims into appropriate episodes of care). This classification is not merely a superficial grouping but involves contextual analysis and understanding of the medical conditions, treatments, procedures, and medications associated with each claim, ensuring that the grouped episodes are logically congruent and clinically meaningful.

The application of episode treatment groupers to the entity data by the processor generates one or more additional data points within a vector of the entity data object which is representative of one or more episode treatment groups. In some embodiments, the value impact platform 120 modifies the entity data object to incorporate one or more episode treatment groups.

In some embodiments, at step 230 the value impact platform 120 generates a verified entity data object based on comparing one or more metrics of the entity data object against one or more predetermined threshold values, wherein entities of the verified entity data object are a subset of the entities of the entity data object.

The verified entity data object is formed by applying one or more filters to the entity data object, thereby identifying and selecting entities deemed to be verified based on one or more conditions and/or thresholds. Each entity within the entity data object, and the data associated with the entity, is compared against a set of predetermined threshold values or criteria. Each threshold value or criterion is associated with one or more data and/or combination of data within the entity data object.

In executing this process, in some embodiments, eligibility and verification are ascertained and/or stored in the entity data object by applying one or more flags to the member data set. These flags act as indicators or markers, signifying the status of each entity concerning one or more eligibility criteria. The criteria for eligibility and verification can encompass a multitude of factors such as enrollment indicators, coverage indicators, age, flags associated with chronic conditions, the number of active prescriptions for the entity, historical indicators, and the like.

Enrollment indicators, for instance, refer to the continuity of an entity's enrollment in one or more programs, ensuring that the entity maintains a consistent and active participation status. The enrollment indicators are related to the entity's past, present, or future enrollment in one or more programs, such as Medicare, Medicaid, an insurance plan, or the like. The enrollment indicators are, in some embodiments, treated as either inclusive or exclusive. For example, entities actively enrolled in a first program are given a verified flag, acting as an inclusive enrollment indicator, while entities actively enrolled in a second program are given an exclusionary flag, acting as an exclusive enrollment indicator where participation in certain programs serves as a basis for excluding the entity from the verified entity data object. Coverage indicators pertain to the medical and prescription coverage attributes of each entity, evaluating the type and extent of coverage available. The coverage indicator is, in some embodiments, categorical, and includes both inclusive and exclusive indicators, similar to the enrollment indicators. The coverage indicator is, in some embodiments, based on one or more coverage metrics, such as the scope of medical coverage and prescription coverage, the network of healthcare providers, the extent of specialized or emergency services included within the coverage, and the like. Further, age criteria are employed to ensure that the entities fall within a specific age bracket, such as above 18 years, ensuring the relevance and applicability of the data and analysis. In some embodiments, one or more flags associated with chronic conditions and the number of active prescriptions are associated with the entities' health status and medical history. In some embodiments, the chronic conditions are indicated by a diagnostic indicator, and the value impact platform 120 identifies non-compliant entities that each have at least one diagnostic indicator associated with respective entity data, the diagnostic indicator being selected from a pre-determined plurality of diagnostic indicators.

In some embodiments, an entity's number of active prescriptions is applied to the entity data object as a threshold value, ensuring that only entities with a specific number of active prescriptions, such as four or more, are considered verified and eligible for further analysis. The value impact platform 120 applies one or more of the filters to the entity data object, verifies entity data and one or more entities, and outputs a verified entity data object which includes the one or more verified entities.

In some embodiments, one or more additional filters are applied to further refine the selection of entities included in the verified entity data object. These additional filters are applied based on data associated with various data sets such as the entity data set, performance history data set, performance metric data sets, and the like. For example, a filter is applied that evaluates the historical performance data of each entity, focusing on patterns, trends, and anomalies that identify the entity's relevance and eligibility based on one or more comparative data metrics. Another filter assesses the correlation between various metrics across different data sets. Yet another filter identifies one or more consistency and/or reliability metrics of the data associated with each entity, ensuring that the entities selected for the verified entity data object exhibit a high degree of data integrity and accuracy.

In some embodiments, at step 240, the value impact platform 120 generates a compliance indicator for each entity of the verified entity data object based on a predetermined ratio value. In some embodiments, the compliance indicator provides a measure of an entity's adherence and/or anticipated adherence to one or more protocols or procedures, or a combination thereof.

Each entity within the verified entity data object is associated with data representing one or more active prescriptions. In some embodiments, each active prescription is associated with a complexity indicator, or score. The complexity indicator is a score or numerical value which indicates the relative intricacy involved in adhering to the prescribed regimen. The complexity indicator is, in some embodiments, inherently tied to or otherwise integrated within the prescription data, or in some embodiments the value impact platform 120 utilizes a complexity data set to assign a complexity to each active prescription associated with the relevant entity in the verified entity data object. In doing so, the value impact platform 120 modifies the verified entity data object to incorporate the complexity indicator for each active prescription. In one embodiment, the complexity score comprises one or more variables, such as the frequency of medication intake, concurrent supplementary medications, historical adherence patterns concerning similar prescriptions, or the like. For example, a medication that is taken once a month is associated with a relatively low complexity score, while a medication that is taken three times a day, along with a supplemental injection once per week has a relatively high complexity score, since it is less likely for a patient to adhere to the program. In some embodiments, the complexity data set is based on historical adherence to a relevant program, and is updated periodically when new adherence data is provided to the system. In some embodiments, the adherences per entity and per regimen is tracked over a first time period, thereby enabling the value impact platform 120 to update complexity scores for the complexity data set.

For each entity, the value impact platform 120 further generates and/or augments an entity total complexity score for each entity. The total complexity score represents a combined or overall complexity score for each entity within the verified entity data object. In some embodiments, the total complexity score is generated based on the complexity score associated with each program (e.g., prescription) of the entity. The total complexity score is, in some embodiments, a summation of the individual program complexity scores. In some embodiments, the value impact platform 120 weights the one or more active utilizations of the entity based on at least one of the one or more performance metric data sets, wherein the weight applied to each active utilization is determined based on the corresponding performance metric data set. For example, a more resource-intensive or difficult active utilization may be given a higher weight to demonstrate its impact on the overall resource utilization.

The value impact platform 120 utilizes the total complexity score for each entity to generate and/or determine an adherence ratio for the entity. The adherence ratio for the entity is an indicator of the portion of days (or any other time units) where the entity is anticipated to be within compliance of their active prescriptions. Compliance, or adherence, is defined as a portion of days (or any other time units) in compliance over a pre-existing threshold, such as 70%. The portion of days covered is related, either proportionally or through an algorithm, to the complexity score. In some embodiments, a high complexity score is associated with a low anticipated compliance.

Various algorithms or associations are utilized by the value impact platform 120 in the evaluation of the adherence ratio for each entity based on the total complexity score. One embodiment involves the value impact platform 120 applying one or more linear algorithms, where the adherence ratio is directly proportional to the complexity score. In this scenario, a linear equation models the relationship, applying coefficients and constants to adjust the influence of the complexity score on the adherence ratio. In some embodiments, the value impact platform 120 incorporates a retrospective model designed to discern patterns of medication adherence. This model processes historical medication regimen data and adherence rates to correlate a complexity score with an adherence ratio to predict adherence likelihood. In some embodiments, the value impact platform 120 employs logistic regression algorithms, predicting the likelihood of an entity's adherence by modeling the log-odds of the binary outcome as a linear combination of the complexity scores. In some embodiments, the value impact platform 120 utilizes decision trees or random forests. Furthermore, in some embodiments, one or more machine-learning models are trained, modified, adjusted, or otherwise configured to intake one or more complexity scores and provide an output that represents an anticipated adherence ratio.

The value impact platform 120 compares the determined and/or generated adherence ratio for each entity against an adherence threshold. The adherence threshold, in some embodiments, is pre-determined by a user of the system, such as 70%, while in some embodiments the threshold is updated dynamically, the dynamic updating based on one or more allocated resources associated with the system, such that the number of entities which surpass the threshold is aligned with a total resource metric associated with the system. The value impact platform 120 then generates a compliance indicator for each entity, wherein the compliance indicator indicates if the entity's adherence exceeds the adherence threshold. Entities which exceed the threshold are flagged as in compliance, while entities which do not exceed the threshold are flagged as non-compliant. The flag is generated as data by the value impact platform 120 and stored in association with the entity data within the verified entity data object.

In some embodiments, at step 250, the value impact platform 120 generates a utilization adjustment data object based on the verified entity data object, a risk score associated with one or more performance metric data sets, and the compliance indicator for each entity. The utilization adjustment data object includes data related to each relevant entity, the complexity of the entity's medication protocol, and a risk group associated with the entity.

The value impact platform 120 performs one or more steps in the generation of the utilization adjustment data object. In some embodiments, the value impact platform 120 maps each entity to one or more pre-defined risk groups. The mapping is based on an episode risk group (ERG) data set. The ERG data set includes information relating to one or more episode groupers and a risk of one or more resource utilizations associated with each episode grouper. By applying the ERG data set to the data associated with each entity, such as previously identified treatment episode groups and/ or active protocols of the entity, the value impact platform 120 generates an ERG risk indicator associated with each entity episode, each entity active protocol, and/or the overall entity. The ERG risk indicator is, in some embodiments, a numerical score across a first range. The ERG risk indicator, in some embodiments, maps the entity to one or more risk categories, which are pre-defined and indicative of a risk profile for the entity.

When calculating the risk score, the value impact platform 120 utilizes one or more metrics associated with one or more active usages related to the entity, such as current prescriptions as discussed herein. As discussed, each active prescription is associated with a complexity score, and the risk score is based in part on one or more complexity scores. Additionally, the total complexity linked with each entity, which includes all active prescriptions and their complexities, also serves as a foundation for the risk score.

In some embodiments, the value impact platform 120 generates the risk score using one or more of retrospective model(s) or machine-learning model(s). The retrospective and/or machine-learning model is trained, modified, adapted, or otherwise configured to identify associations between data associated with one or more active utilizations and compliance risk. The model is updated as new data becomes available to the system, which further tunes and/or adjusts the model based on the received data. The retrospective and/or machine-learning model outputs a risk score associated with the entity, and the risk score is incorporated into one or more data objects, such as the utilization adjustment data object.

Based on one or more of the data received or generated by the value impact platform 120, the value impact platform 120 engages in the assignment of one or more interventions to each entity. These interventions are, in some embodiments, generated based on one or more data vectors, including but not limited to, the risk group to which the entity has been allocated, as well as existing protocols, utilizations, and prescriptions related to the entity. Specifically, the healthcare management module 126 invokes the healthcare management model 127, which is configured to be inclusive of algorithmic, retrospective, and/or machine-learning models, or a hybrid combination of multiple discrete models and algorithms.

The intervention aims to effectuate a calculated alteration in one or more active protocols, utilizations, or prescriptions associated with the entity, and achieves a dual objective: to reduce the total complexity score associated with the entity's healthcare utilizations and to enhance the entity's compliance metrics. Within the scope of the intervention, a data object is formulated to encompass information related to the entity's pre-intervention compliance level as well as a predictive model indicating the likely post-intervention compliance level. This predictive model relies substantially on the complexity of the entity's healthcare protocol after the intervention has been implemented.

Within the intervention data object is a utilization offset metric. The utilization offset metric serves as a quantitative or qualitative indicator, highlighting the anticipated offset in resource utilizations and/or resultant cost consequent to the implementation of the intervention. The term "resource" is broadly defined herein to encapsulate various types of healthcare-related utilizations. These could range from general healthcare utilizations to specialized categories such as emergency department utilizations, inpatient visit utilizations, or even cost utilizations attributable to non-compliance, or the like.

The utilization offset metric is not constrained to cost or resource utilization parameters. The utilization offset metric is structured to include metrics that also portray expected improvements in healthcare outcomes. These outcome improvements are linked to both the pre-intervention and the post-intervention compliance levels of the entity. For example, if an entity initially demonstrates poor adherence to medication protocols, the post-intervention predictive model might indicate a probable increase in medication adherence, and the utilization offset metric will consequently capture the expected decline in emergency department visits or other acute care needs, which is indicative of improved entity care outcomes.

Subsequent to the assignment of interventions, the value impact platform 120 utilizes one or more of the aforementioned data to generate a data structure known as the utilization adjustment data object. The utilization adjustment data object encompasses each of the verified entities that have been subject to the risk assessment and intervention assignment processes. Within the utilization adjustment data object, pertinent details associated with each verified entity are organized and stored in one or more vectors or other data arrays. This includes, but is not limited to, risk group classifications, complexity scores, pre-intervention and post-intervention compliance levels, as well as the corresponding utilization offset metrics.

In some embodiments, at step 260, the value impact platform 120 causes the utilization adjustment data object to be displayed on a Graphical User Interface (GUI). The displayed data includes one or more of risk groups, complexity scores, compliance indicators, intervention details, and utilization offset metrics, among others—that have been calculated or otherwise generated by the value impact platform 120 for each verified entity. The GUI layout is configured to permit navigational ease, enabling users to explore individual aspects of the data object, conduct comparative analyses, and possibly adjust or refine interventions. The display of the utilization data object is, in some embodiments, in the form of a structured data format, including one or more sorting and/or filter options.

In some embodiments, the GUI of the value impact platform 120 incorporates a scenario modeling function, enabling users to simulate various scenarios and predict potential outcomes based on the data present within or received by the system. The scenario modeling process and results can be presented to the user visually through the GUI. This scenario modeling function enables healthcare providers and administrators to input different variables or modify existing parameters, and then observe the anticipated effects on resource utilization, intervention efficacy, or other relevant metrics. For instance, a user could model the outcome of a new intervention strategy on a specific patient subgroup, or predict resource utilization shifts in response to environmental changes. This scenario-based approach facilitates proactive planning, as stakeholders can test hypotheses, anticipate challenges, and strategize interventions in a virtual environment before actual implementation, ensuring informed and data-driven decision-making processes. In some embodiments, the value impact platform 120 receives one or more input from the user indicative of a user preference, then updates the displayed data and/or adjusts one or more thresholds or weights associated with one or more prior steps to generate one or more updated system outputs associated with the one or more preferences of the user.

In some embodiments, one or more intervention data objects and/or arrays are generated. For each member, one or more interventions are assigned to the member. The intervention, in some embodiments, is associated with one or more alternative paths of care, which are associated with a particular resource utilization. The intervention is assigned by the value impact platform 120 utilizing one or more of machine-learning model(s), retrospective model(s), or other algorithms to output an intervention that results in the most efficient resource utilization, such as by suggesting an intervention by altering one or more active utilizations of the member to an alternative utilization based on one or more member data, the likelihood of success of the intervention, the expected resource utilization (such as cost) of the intervention, and the overall reduction in resource utilization of the alternative care pathway.

Interventions are of varied types and include but are not limited to medication management, virtual nurse consultations, in-home support services, and mental health assessments. These interventions are not limited to re-admission, resource utilization, medication, or like issues and encompass a range of healthcare needs. The interventions are applied either at a member-level or at a data object level, such as applied to one or more group of entities or members. When applied at a member-level, each member receives a personalized recommended interventions based on their medical history, risk factors, and other variables such as geographic location or distance to hospital. The intervention is applied as a flag to the entity data object. When applied at a group level, all members of the particular group receive a common set of interventions optimized for that group's average or median characteristics.

The generation of interventions also incorporates an efficiency metric that accounts for the effectiveness of the interventions in reducing unnecessary resource utilizations, such as medication adherence. This efficiency metric is quantified in terms of reduction in readmissions, and is often balanced against the cost of the intervention to ensure that the overall healthcare system achieves cost savings.

In some embodiments, the success of one or more interventions is tracked by the value impact platform 120. Tracking involves the monitoring and recording of target performance indicators such as medication complexity, resource utilization rate, patient satisfaction, and overall healthcare cost reduction. The collected data is subsequently used to refine the healthcare management model 127 for future scenario modeling predictions. Specifically, the realized success rates of the interventions are incorporated into the model's underlying algorithms, enabling the model to adapt and improve its accuracy in generating subsequent interventions. The ongoing integration of real-world performance data thus contributes to the continual calibration of the healthcare management model 127, thereby facilitating more precise and efficient allocation of healthcare resources and better targeting of alternative care pathways.

In some embodiments, the value impact platform 120 employs a scenario modeling technique to determine one or more possible effects of a determined intervention action on internal system utilization or intervention efficacy. The scenario modeling technique generates one or more scenario model data objects. The scenario model data object is structured to encapsulate distinct recommended focus areas, for instance, specified interventions that propel the overall member population toward particular population states. These population states are selected for their alignment with defined objectives that are stored within the scenario model data object and/or within value impact platform 120. The objectives include, but are not limited to, precise metrics such as the medication adherence, optimization of resource allocation, quantifiable reduction in readmission rates, measurable changes in patient health outcomes, and minimization of healthcare-related expenditures.

The generation of these scenario model data objects is facilitated by the value impact platform 120, through the data processing module 124 and the healthcare management module 126. By leveraging data from health data 110 and other relevant sources, the scenario modeling system analyzes, evaluates, and predicts the potential impact of specific interventions or changes within the network environment 100.

In some embodiments, scenario modeling is executed by assigning one or more weight values to one or more metrics or outcomes associated with one or more of the data sets, to generate an optimized strategy for the healthcare system. These metrics or outcomes include, in some embodiments, a first metric such as the rate of resource utilization, a second metric such as patient readmission rates, and further metrics pertaining to patient care outcomes and cost efficiency as described herein. Each metric is attributed a specific weight that reflects its relative importance or anticipated influence on the system's overarching aims. The assignment of these weights may be initially established based on empirical healthcare data, benchmarks prevalent within the healthcare industry, or the expertise of healthcare practitioners or system administrators. Furthermore, the scenario modeling system is configured to recalibrate these weights automatically in response to shifts in population health trends or modifications in healthcare delivery contracts, such as by applying a goal-seeking algorithm and iteratively modeling varying intervention scenarios. Alternatively, the system allows for manual adjustment of these weight values by authorized users, thereby providing a dual mechanism for dynamic weight adjustment. The weighting of metrics or outcomes allows the scenario modeling system to balance multiple considerations, such as clinical effectiveness, cost-efficiency, patient satisfaction, patient compliance, regulatory compliance, and the like. For example, if the healthcare system aims to reduce resource utilization via reduction of medication complexity and improving adherence while maintaining a high level of patient satisfaction, the scenario modeling system can adjust the weights assigned to these outcomes to find a suitable balance of utilization reduction and alternative care pathway adoption, which in some embodiments would signify patient satisfaction with their medical care.

The user interface module 128 provides a comprehensive visualization of the scenario model data object. It allows users, such as healthcare professionals or administrators, to interact with the data, modify parameters or assumptions, and view updated projections in real-time. This interaction enables the identification of key strategies that can drive desired outcomes and optimize the healthcare system's overall performance.

Once the weights are assigned, the scenario modeling system utilizes the healthcare management model 127, which encompasses various algorithms or machine-learning models, to analyze the data and generate predictions. The system considers the relationships between different variables, the potential impact of interventions, and the feasibility of achieving desired outcomes based on the current state of the healthcare system, such as free resources.

Additionally, the scenario modeling system enables users to simulate various scenarios by adjusting the weights of metrics or outcomes, altering assumptions, or modifying input data. This flexibility allows for a thorough exploration of different strategies and their potential outcomes, helping decision-makers to make informed choices that align with the healthcare system's objectives. Furthermore, the scenario modeling system incorporates feedback loops for continuous improvement. As real-world data is collected and analyzed, the system refines its models and adjusts the weights of metrics or outcomes to reflect the most current and accurate information. Furthermore, the scenario modeling system considers external factors, such as changing regulatory requirements, socio-economic conditions, or advancements in medical technology. This ensures that the system remains adaptive and forward-looking, aligning with the evolving needs of the network environment 100 and the members.

In some embodiments, the value impact platform 120 performs model monitoring. Model monitoring includes assessment one or more model performance metrics and detecting drift in the change in the statistical properties of the data that was used to train the data. In some embodiments, the drift is associated with the interventions impact on the population, as the interventions prove successful the resulting member population metrics will, in some embodiments, drift from the metrics of the starting population. This drift, in some embodiments, is detected as new health data is populated into the system. The value impact platform 120 tracks initial parameters and/or metrics associated with the member data object and identifies changes and/or differences in those parameters over time as new data is populated into the system.

In some embodiments, the value impact platform 120 includes one or more correction mechanisms in response to the detected drift, aiming to adjust and optimize the model for altered data patterns and distributions. These correction mechanisms involve adaptive algorithms that modify model parameters, weight adjustments, or feature recalibration, ensuring that the model remains aligned with the evolving nature of the input data. In certain embodiments, the correction mechanisms employ techniques such as reinforcement learning, transfer learning, or online learning to swiftly adapt to the changing data landscape. Furthermore, these mechanisms might trigger model retraining processes, wherein new data is utilized to update the model, thereby enhancing its predictive accuracy and reliability. In other embodiments, when significant drift is detected, the correction mechanisms might recommend a comprehensive overhaul of the model, encompassing the incorporation of novel features, adjustment of hyperparameters, or even the selection of an alternative modeling approach, thereby maintaining the model's efficacy in dynamically changing environments.

In some embodiments, the value impact platform 120 includes a fairness monitoring to ensure equitable model performance across diverse populations. The value impact platform 120 systematically compares selection rates between predicted outcomes and training data, focusing on attributes including but not limited to gender, age, Area Deprivation Index (ADI) codes, Rural-Urban Commuting Area (RUCA) codes, and Social Determinants of Health (SDOH) Socioeconomic Status (SES) metrics. The fairness monitoring process identifies and mitigates biases, ensuring that the model's predictions do not disproportionately favor or disadvantage any group based on these sensitive features. In some embodiments, the value impact platform 120 includes one or more correction mechanisms in response to fairness modeling. In some embodiments, upon detection of bias or drift through the fairness monitoring component, the value impact platform 120 initiates corrective measures to adjust the model. These measures may include retraining the model with augmented datasets, applying algorithmic fairness techniques, or adjusting predictive thresholds. The platform is configured to automatically implement such corrections to ensure that model outputs remain in alignment with one or more predefined fairness criteria, such as equal opportunity, demographic parity, or the like.

Figure 3:
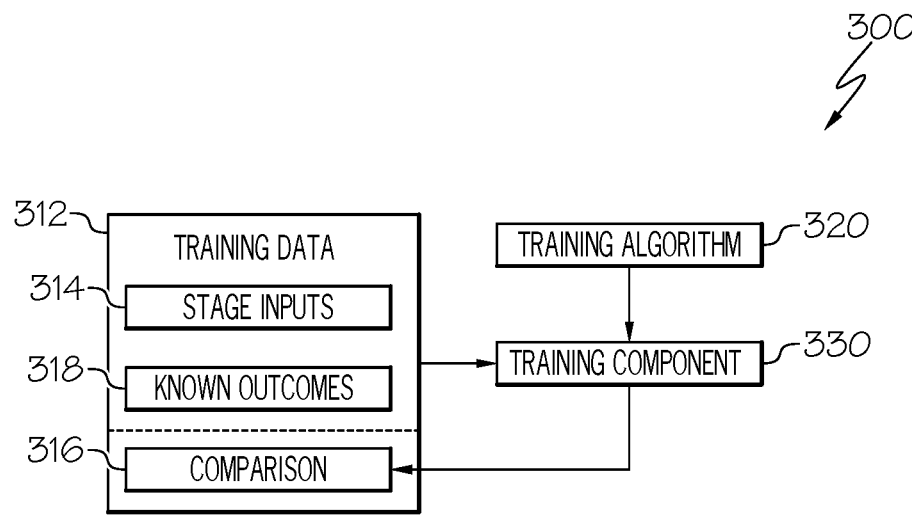
FIG. 3 shows an example model training flow chart, according to some embodiments of the disclosure.

One or more implementations disclosed herein include and/or are implemented using a machine-learning model. For example, one or more of the modules of the value impact platform are implemented using a machine-learning model and/or are used to train the machine-learning model. FIG. 3 shows an example machine-learning training flow chart, according to some embodiments of the disclosure. Referring to FIG. 3, a given machine-learning model is trained using the training flow chart 300. The training data 312 includes one or more of stage inputs 314 and the known outcomes 318 related to the machine-learning model to be trained. The stage inputs 314 are from any applicable source including text, visual representations, data, values, comparisons, and stage outputs, e.g., one or more outputs from one or more steps from FIG. 2. The known outcomes 318 are included for the machine-learning models generated based on supervised or semi-supervised training, or can based on known labels, such as topic labels. An unsupervised machine-learning model is not trained using the known outcomes 318. The known outcomes 318 includes known or desired outputs for future inputs similar to or in the same category as the stage inputs 314 that do not have corresponding known outputs.

The training data 312 and a training algorithm 320, e.g., one or more of the modules implemented using the machine-learning model and/or are used to train the machine-learning model, is provided to a training component 330 that applies the training data 312 to the training algorithm 320 to generate the machine-learning model. According to an implementation, the training component 330 is provided comparison results 316 that compare a previous output of the corresponding machine-learning model to apply the previous result to re-train the machine-learning model. The comparison results 316 are used by the training component 330 to update the corresponding machine-learning model. The training algorithm 320 utilizes machine-learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, classifiers such as K-Nearest Neighbors, and/or discriminative models such as Decision Forests and maximum margin methods, the model specifically discussed herein, or the like.

The machine-learning model used herein is trained and/or used by adjusting one or more weights and/or one or more layers of the machine-learning model. For example, during training, a given weight is adjusted (e.g., increased, decreased, removed) based on training data or input data. Similarly, a layer is updated, added, or removed based on training data/and or input data. The resulting outputs are adjusted based on the adjusted weights and/or layers.

In general, any process or operation discussed in this disclosure is understood to be computer-implementable, such as the process illustrated in FIG. 2 are performed by one or more processors of a computer system as described herein. A process or process step performed by one or more processors is also referred to as an operation. The one or more processors are configured to perform such processes by having access to instructions (e.g., software or computer-readable code) that, when executed by one or more processors, cause one or more processors to perform the processes. The instructions are stored in a memory of the computer system. A processor is a central processing unit (CPU), a graphics processing unit (GPU), or any suitable type of processing unit.

A computer system, such as a system or device implementing a process or operation in the examples above, includes one or more computing devices. One or more processors of a computer system are included in a single computing device or distributed among a plurality of computing devices. One or more processors of a computer system are connected to a data storage device. A memory of the computer system includes the respective memory of each computing device of the plurality of computing devices.

Figure 4:
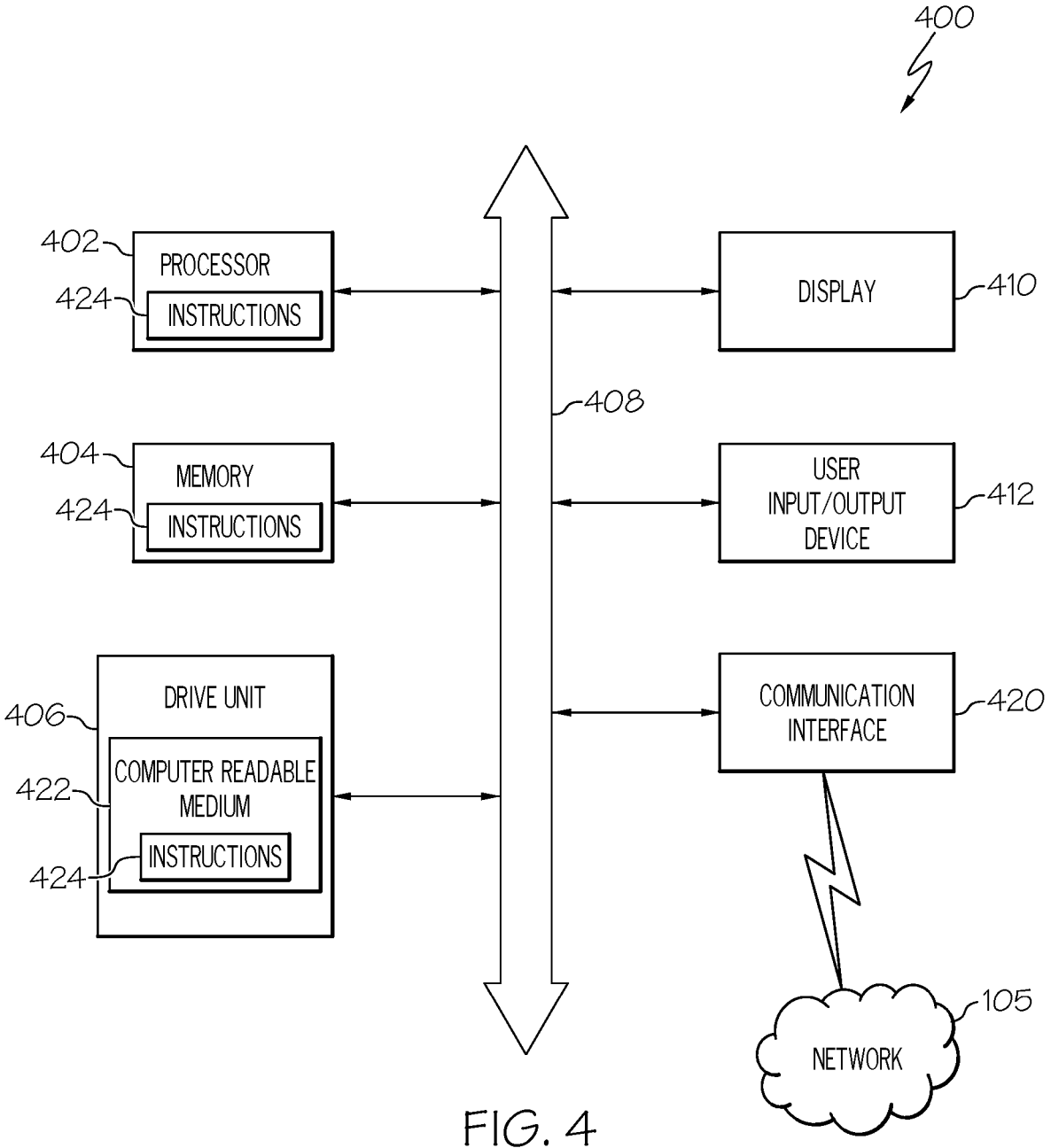
FIG. 4 illustrates an implementation of a computer system that executes techniques presented herein, according to some embodiments of the disclosure.

FIG. 4 illustrates an implementation of a computer system that executes techniques presented herein. The computer system 400 includes a set of instructions that are executed to cause the computer system 400 to perform any one or more of the methods or computer based functions disclosed herein. The computer system 400 operates as a standalone device or is connected, e.g., using a network, to other computer systems or peripheral devices.

Unless specifically stated otherwise, as apparent from the following discussions, it is appreciated that throughout the specification, discussions utilizing terms such as "processing," "computing," "calculating," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" refers to any device or portion of a device that processes electronic data, e.g., from registers and/or memory to transform that electronic data into other electronic data that, e.g., is stored in registers and/or memory. A "computer," a "computing machine," a "computing platform," a "computing device," or a "server" includes one or more processors.

In a networked deployment, the computer system 400 operates in the capacity of a server or as a client user computer in a server-client user network environment, or as a peer computer system in a peer-to-peer (or distributed) network environment. The computer system 400 is also implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular implementation, the computer system 400 is implemented using electronic devices that provide voice, video, or data communication. Further, while the computer system 400 is illustrated as a single system, the term "system" shall also be taken to include any collection of systems or sub-systems that individually or jointly execute a set, or multiple sets, of instructions to perform one or more computer functions.

As illustrated in FIG. 4, the computer system 400 includes a processor 402, e.g., a central processing unit (CPU), a graphics processing unit (GPU), or both. The processor 402 is a component in a variety of systems. For example, the processor 402 is part of a standard personal computer or a workstation. The processor 402 is one or more processors, digital signal processors, application specific integrated circuits, field programmable gate arrays, servers, networks, digital circuits, analog circuits, combinations thereof, or other now known or later developed devices for analyzing and processing data. The processor 402 implements a software program, such as code generated manually (i.e., programmed).

The computer system 400 includes a memory 404 that communicates via bus 408. The memory 404 is a main memory, a static memory, or a dynamic memory. The memory 404 includes, but is not limited to computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory 404 includes a cache or random-access memory for the processor 402. In alternative implementations, the memory 404 is separate from the processor 402, such as a cache memory of a processor, the system memory, or other memory. The memory 404 is an external storage device or database for storing data. Examples include a hard drive, compact disc ("CD"), digital video disc ("DVD"), memory card, memory stick, floppy disc, universal serial bus ("USB") memory device, or any other device operative to store data. The memory 404 is operable to store instructions executable by the processor

402. The functions, acts, or tasks illustrated in the figures or described herein are performed by the processor 402 executing the instructions stored in the memory 404. The functions, acts, or tasks are independent of the particular type of instruction set, storage media, processor, or processing strategy and are performed by software, hardware, integrated circuits, firmware, micro-code, and the like, operating alone or in combination. Likewise, processing strategies include multiprocessing, multitasking, parallel processing, and the like.

As shown, the computer system 400 further includes a display 410, such as a liquid crystal display (LCD), an organic light emitting diode (OLED), a flat panel display, a solid-state display, a cathode ray tube (CRT), a projector, a printer or other now known or later developed display device for outputting determined information. The display 410 acts as an interface for the user to see the functioning of the processor 402, or specifically as an interface with the software stored in the memory 404 or in the drive unit 406.

Additionally or alternatively, the computer system 400 includes an input/output device 412 configured to allow a user to interact with any of the components of the computer system 400. The input/output device 412 is a number pad, a keyboard, a cursor control device, such as a mouse, a joystick, touch screen display, remote control, or any other device operative to interact with the computer system 400.

The computer system 400 also includes the drive unit 406 implemented as a disk or optical drive. The drive unit 406 includes a computer-readable medium 422 in which one or more sets of instructions 424, e.g. software, is embedded. Further, the sets of instructions 424 embodies one or more of the methods or logic as described herein. The sets of instructions 424 resides completely or partially within the memory 404 and/or within the processor 402 during execution by the computer system 400. The memory 404 and the processor 402 also include computer-readable media as discussed above.

In some systems, computer-readable medium 422 includes the set of instructions 424 or receives and executes the set of instructions 424 responsive to a propagated signal so that a device connected to network 105 communicates voice, video, audio, images, or any other data over the network 105. Further, the sets of instructions 424 are transmitted or received over the network 105 via the communication port or interface 420, and/or using the bus 408. The communication port or interface 420 is a part of the processor 402 or is a separate component. The communication port or interface 420 is created in software or is a physical connection in hardware. The communication port or interface 420 is configured to connect with the network 105, external media, the display 410, or any other components in the computer system 400, or combinations thereof. The connection with the network 105 is a physical connection, such as a wired Ethernet connection, or is established wirelessly as discussed below. Likewise, the additional connections with other components of the computer system 400 are physical connections or are established wirelessly. The network 105 alternatively be directly connected to the bus 408.

While the computer-readable medium 422 is shown to be a single medium, the term "computer-readable medium" includes a single medium or multiple media, such as a centralized or distributed database, and/or associated caches and servers that store one or more sets of instructions. The term "computer-readable medium" also includes any medium that is capable of storing, encoding, or carrying a set of instructions for execution by a processor or that causes a computer system to perform any one or more of the methods or operations disclosed herein. The computer-readable medium 422 is non-transitory, and may be tangible.

The computer-readable medium 422 includes a solid-state memory such as a memory card or other package that houses one or more non-volatile read-only memories. The computer-readable medium 422 is a random-access memory or other volatile re-writable memory. Additionally or alternatively, the computer-readable medium 422 includes a magneto-optical or optical medium, such as a disk or tapes or other storage device to capture carrier wave signals such as a signal communicated over a transmission medium. A digital file attachment to an e-mail or other self-contained information archive or set of archives is considered a distribution medium that is a tangible storage medium. Accordingly, the disclosure is considered to include any one or more of a computer-readable medium or a distribution medium and other equivalents and successor media, in which data or instructions are stored.

In an alternative implementation, dedicated hardware implementations, such as application specific integrated circuits, programmable logic arrays, and other hardware devices, is constructed to implement one or more of the methods described herein. Applications that include the apparatus and systems of various implementations broadly include a variety of electronic and computer systems. One or more implementations described herein implement functions using two or more specific interconnected hardware modules or devices with related control and data signals that are communicated between and through the modules, or as portions of an application-specific integrated circuit. Accordingly, the present system encompasses software, firmware, and hardware implementations.

Computer system 400 is connected to the network 105. The network 105 defines one or more networks including wired or wireless networks. The wireless network is a cellular telephone network, an 802.10, 802.16, 802.20, or WiMAX network. Further, such networks include a public network, such as the Internet, a private network, such as an intranet, or combinations thereof, and utilizes a variety of networking protocols now available or later developed including, but not limited to TCP/IP based networking protocols. The network 105 includes wide area networks (WAN), such as the Internet, local area networks (LAN), campus area networks, metropolitan area networks, a direct connection such as through a Universal Serial Bus (USB) port, or any other networks that allows for data communication. The network 105 is configured to couple one computing device to another computing device to enable communication of data between the devices. The network 105 is generally enabled to employ any form of machine-readable media for communicating information from one device to another. The network 105 includes communication methods by which information travels between computing devices. The network 105 is divided into sub-networks. The sub-networks allow access to all of the other components connected thereto or the sub-networks restrict access between the components. The network 105 is regarded as a public or private network connection and includes, for example, a virtual private network or an encryption or other security mechanism employed over the public Internet, or the like.

In accordance with various implementations of the present disclosure, the methods described herein are implemented by software programs executable by a computer system. Further, in an example, non-limited implementation, implementations can include distributed processing, component/object distributed processing, and parallel processing. Alternatively, virtual computer system processing can be constructed to implement one or more of the methods or functionality as described herein.

Although the present specification describes components and functions that are implemented in particular implementations with reference to particular standards and protocols, the disclosure is not limited to such standards and protocols. For example, standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

It will be understood that the steps of methods discussed are performed in one embodiment by an appropriate processor (or processors) of a processing (i.e., computer) system executing instructions (computer-readable code) stored in storage. It will also be understood that the disclosure is not limited to any particular implementation or programming technique and that the disclosure is implemented using any appropriate techniques for implementing the functionality described herein. The disclosure is not limited to any particular programming language or operating system.

It should be appreciated that in the above description of example embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the disclosure.

In the description provided herein, numerous specific details are set forth. However, it is understood that embodiments of the disclosure are practiced without these specific details. In other instances, well-known methods, structures and techniques have not been shown in detail in order not to obscure an understanding of this description.

Thus, while there has been described what are believed to be the preferred embodiments of the disclosure, those skilled in the art will recognize that other and further modifications are made thereto without departing from the spirit of the disclosure, and it is intended to claim all such changes and modifications as falling within the scope of the disclosure. For example, any formulas given above are merely representative of procedures that may be used. Functionality may be added or deleted from the block diagrams and operations may be interchanged among functional blocks. Steps may be added or deleted to methods described within the scope of the present disclosure.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

The present disclosure furthermore relates to the following aspects:

Example 1. A computer-implemented method comprising: receiving, by one or more processors, a first data object, the first data object including: an entity data set containing a plurality of entities; a performance history data set containing a plurality of performance-related records; an event data set; and one or more performance metric data sets; generating, by the one or more processors, an entity data object based on at least one of the entity data set, the performance history data set, or the one or more performance metric data sets; generating, by the one or more processors, a verified entity data object based on comparing one or more metrics of the entity data object against one or more predetermined threshold values, wherein entities of the verified entity data object are a subset of the entities of the entity data object; generating, by the one or more processors, a compliance indicator for each entity of the verified entity data object; generating, by the one or more processors, a utilization adjustment data object based on the verified entity data object, a risk score associated with one or more performance metric data sets, and the compliance indicator for each entity; and causing, by the one or more processors, the utilization adjustment data object to be displayed on a Graphical User Interface (GUI).

Example 2. The computer-implemented method of Example 1, further comprising: generating, by the one or more processors, a risk score associated with one or more performance metric data sets by applying a retrospective model to the verified entity data object, the retrospective model configured to identify one or more correlations between active prescriptions and risk of non-compliance; and receiving, by the one or more processors, the risk score from the retrospective model.

Example 3. The computer-implemented method of Example 2, further comprising: adjusting, by the one or more processors, the retrospective model, the adjusting based on an identified drift between the first data object and an updated data object received by the one or more processors.

Example 4. The computer-implemented method of any of Examples 1-3, wherein generating the verified entity data object comprises identifying entities that meet one or more utility criteria based the entity data set.

Example 5. The computer-implemented method of any of Examples 1-4, wherein the risk score is based on one or more active utilizations of an entity.

Example 6. The computer-implemented method of Example 5, further comprising: weighting, by the one or more processors, the one or more active utilizations of the entity based on at least one of the one or more performance metric data sets, wherein a weight applied to each active utilization is determined based on a corresponding performance metric data set.

Example 7. The computer-implement method of any of Examples 1-6, wherein generating the compliance indicator includes: receiving a complexity score for each active prescription associated with each entity in the verified entity data object; assigning a total complexity score to each entity, said total complexity score representing a cumulative measure of the complexity scores of all active prescriptions associated with the entity; determining an adherence ratio for each entity using the total complexity score for the entity, the adherence ratio indicative of an expected proportion of days the entity is in compliance with an active prescription regimen; comparing the adherence ratio of each entity against an adherence threshold; and generating a compliance indicator for each entity, wherein entities meeting or surpassing the adherence threshold are marked as compliant, and entities falling below the adherence threshold are marked as non-compliant.

Example 8. The computer-implemented method of any of Examples 1-7, further comprising: identifying, by the one or more processors, non-compliant entities that each have at least one diagnostic indicator associated with respective entity data, the diagnostic indicator being selected from a pre-determined plurality of diagnostic indicators.

Example 9. The computer-implement method of Example 8, wherein the at least one diagnostic indicator is a chronic condition.

Example 10. A system comprising memory and one or more processors communicatively coupled to the memory, the one or more processors configured to: receive a first data object, the first data object including: an entity data set containing a plurality of entities; a performance history data set containing a plurality of performance-related records; an event data set; and one or more performance metric data sets; generate an entity data object based on at least one of the entity data set, the performance history data set, or the one or more performance metric data sets; generate a verified entity data object based on comparing one or more metrics of the entity data object against one or more predetermined threshold values, wherein entities of the verified entity data object are a subset of the entities of the entity data object; generate a compliance indicator for each entity of the verified entity data object; generate a utilization adjustment data object based on the verified entity data object, a risk score associated with one or more performance metric data sets, and the compliance indicator for each entity; and cause the utilization adjustment data object to be displayed on a Graphical User Interface (GUI).

Example 11. The system of Example 10, the processor further configured to: generate a risk score by applying a retrospective model to the verified entity data object, the retrospective model configured to identify one or more correlations between active prescriptions and risk of non-compliance; and receive the risk score from the retrospective model.

Example 12. The system of Example 11, the processor further configured to: adjust the retrospective model, the adjusting based on an identified drift between the first data object and an updated data object received by the one or more processors.

Example 13. The system of any of Examples 10-12, wherein generating the verified entity data object comprises identifying entities that meet one or more utility criteria based the entity data set.

Example 14. The system of any of Examples 10-13, wherein the risk score is based on one or more active utilizations of an entity.

Example 15. The system of Example 14, the processor further configured to: apply a weight to the one or more active utilizations of the entity based on at least one of the one or more performance metric data sets, wherein a weight applied to each active utilization is determined based on a corresponding performance metric data set.

Example 16. The system of any of Examples 10-15, wherein generating the compliance indicator includes: receiving a complexity score for each active prescription associated with each entity in the verified entity data object; assigning a total complexity score to each entity, said total complexity score representing a cumulative measure of the complexity scores of all active prescriptions associated with the entity; determining an adherence ratio for each entity using the total complexity score for the entity, the adherence ratio indicative of an expected proportion of days the entity is in compliance with an active prescription regimen; comparing the adherence ratio of each entity against an adherence threshold; and generating a compliance indicator for each entity, wherein entities meeting or surpassing the adherence threshold are marked as compliant, and entities falling below the adherence threshold are marked as non-compliant.

Example 17. The system of any of Examples 10-16, the processor further configured to: identify non-compliant entities that each have at least one diagnostic indicator associated with respective entity data, the diagnostic indicator being selected from a pre-determined plurality of diagnostic indicators.

Example 18. The system of Example 17, wherein the at least one diagnostic indicator is a chronic condition.

Example 19. One or more non-transitory computer-readable storage media including instructions that, when executed by one or more processors, cause the one or more processors to: receive a first data object, the first data object including: an entity data set containing a plurality of entities; a performance history data set containing a plurality of performance-related records; an event data set; and one or more performance metric data sets; generate an entity data object based on at least one of the entity data set, the performance history data set, or the one or more performance metric data sets; generate a verified entity data object based on comparing one or more metrics of the entity data object against one or more predetermined threshold values, wherein entities of the verified entity data object are a subset of the entities of the entity data object; generate a compliance indicator for each entity of the verified entity data object; generate a utilization adjustment data object based on the verified entity data object, a risk score associated with one or more performance metric data sets, and the compliance indicator for each entity; and cause the utilization adjustment data object to be displayed on a Graphical User Interface (GUI).

Example 20. The one or more non-transitory computer-readable storage media of Example 19, wherein generating the compliance indicator includes: receiving a complexity score for each active prescription associated with each entity in the verified entity data object; assigning a total complexity score to each entity, said total complexity score representing a cumulative measure of the complexity scores of all active prescriptions associated with the entity; determining an adherence ratio for each entity using the total complexity score for the entity, the adherence ratio indicative of an expected proportion of days the entity is in compliance with an active prescription regimen; comparing the adherence ratio of each entity against an adherence threshold; and generating a compliance indicator for each entity, wherein entities meeting or surpassing the adherence threshold are marked as compliant, and entities falling below the adherence threshold are marked as non-compliant.

What is claimed is:

1. A computer-implemented method comprising:
receiving, by one or more processors, a first data object, the first data object including:
an entity data set including a plurality of entities;
a performance history data set including a plurality of performance-related records for the plurality of entities; and
one or more performance metric data sets for the plurality of entities,
including active utilization data of the plurality of entities;
generating, by the one or more processors, an entity data object for individual entities of the plurality of entities based on at least one of the entity data set, the performance history data set, or the one or more performance metric data sets;
identifying, by the one or more processors and based on the entity data object for the individual entities of the plurality of entities, a subset of entities, of the plurality of entities, having a medication protocol for medical condition management that satisfies an eligibility criterion;
determining, by the one or more processors and using a machine learning model, a risk score for the individual entities of the subset of entities based on the one or more performance metric data sets included in the first data object, wherein the machine learning model is trained, based on training data, to (i) identify associations between the active utilization data and a compliance risk for the individual entities of the subset of entities and (ii) output the risk score representing the compliance risk based on the identified associations;
generating, by the one or more processors and based on the entity data object for the individual entities of the subset of entities, a compliance indicator indicating a likelihood of adherence of the respective individual entities of the subset of entities to the medication protocol;
generating, by the one or more processors and based on the entity data object and the compliance indicator, an intervention data object for the respective individual entities of the subset of entities that includes a targeted alteration to the medication protocol;
generating, by the one or more processors, a utilization adjustment data object based on the entity data object, the risk score, the compliance indicator, and the intervention data object for the respective individual entities of the subset of entities, wherein the respective individual entities of the subset of entities are mapped to one of a plurality of risk groups in the utilization adjustment data object;

causing, by the one or more processors, the utilization adjustment data object to be displayed on a Graphical User Interface (GUI);

in response to determining at least one individual entity of the subset of entities being mapped to a particular risk group of the plurality of risk groups, applying, by the one or more processors, the targeted alteration to the medication protocol for the at least one individual entity to cause administration of an altered medication protocol to the at least one individual entity, the altered medication protocol including the targeted alteration;

monitoring, by the one or more processors, a performance of the machine learning model as a new data object is received;

detecting, by the one or more processors and based on the monitoring, parameters associated with the new data object having a threshold difference from parameters associated with the training data that indicate a drift, the drift affecting the performance of the machine learning model; and in response to detecting the drift, applying, by the one or more processors, a correction mechanism to optimize the performance of the machine learning model, the correction mechanism including a retraining of the machine learning model based on the parameters associated with the new data object.

2. The computer-implemented method of claim 1, wherein the active utilization data includes one or more active prescriptions of the medication protocol.

3. The computer-implemented method of claim 1, wherein determining the risk score further comprises:

weighting, by the one or more processors, one or more active utilizations included in the active utilization data for the individual entities of the subset of entities based on at least one of the one or more performance metric data sets, wherein a weight applied to each active utilization is determined based on a corresponding performance metric data set.

4. The computer-implemented method of claim 1, wherein the medication protocol for the individual entities of the subset of entities includes one or more active prescriptions associated with each respective individual entity and generating the compliance indicator includes:

receiving a complexity score for each active prescription of the one or more active prescriptions;

assigning a total complexity score, the total complexity score representing a cumulative measure of the complexity score for each active prescription of the one or more active prescriptions;

determining an adherence ratio using the total complexity score, the adherence ratio indicative of an expected proportion of days the respective individual entity is in compliance with an active prescription regimen of the medication protocol;

comparing the adherence ratio against an adherence threshold; and generating the compliance indicator, wherein a first portion of the individual entities of the subset of entities meeting or surpassing the adherence threshold are marked as compliant, and a second portion of the individual entities of the subset of entities falling below the adherence threshold are marked as non-compliant.

5. The computer-implemented method of claim 1, wherein identifying the subset of entities further comprises:

identifying, by the one or more processors, the individual entities of the subset of entities as having at least one diagnostic indicator for a medical condition associated with the entity data object, the at least one diagnostic indicator being selected from a pre-determined plurality of diagnostic indicators.

6. The computer-implemented method of claim 5, wherein the at least one diagnostic indicator is for a chronic medical condition.

7. The computer-implemented method of claim 1, wherein generating the intervention data object for the respective individual entities of the subset of entities comprises:

generating, by the one or more processors, the targeted alteration to the medication protocol to increase the likelihood of adherence to the medication protocol and reduce resource utilization by the respective individual entities of the subset of entities.

8. The computer-implemented method of claim 1, wherein generating the intervention data object for the respective individual entities of the subset of entities comprises:

determining a utilization offset metric associated with an expected reduction in resource utilizations by the respective individual entities in response to the targeted alteration to the medication protocol, wherein the utilization offset metric is included in the intervention data object.

9. The computer-implemented method of claim 1, wherein the entity data object for the individual entities of the subset of entities includes information for one or more active prescriptions associated with the medication protocol, metrics indicating historical adherence to the medication protocol, and one or more external factors affecting adherence to the medication protocol.

10. The computer-implemented method of claim 1, wherein the correction mechanism including the retraining of the machine learning model is a first correction mechanism applied when the detected drift is below a threshold.

11. The computer-implemented method of claim 10, wherein when the detected drift is above the threshold, applying the correction mechanism further comprises:

applying a second correction mechanism including one or more of incorporation of novel features or adjustment of hyperparameters of the machine learning model.

12. The computer-implemented method of claim 1, wherein the retraining of the machine learning model includes one or more of modifying model parameters, adjusting weights, or recalibrating features.

13. A system comprising:

one or more processors; and one or more non-transitory computer readable media storing processor-executable instructions which, when executed by the one or more processors, cause the one or more processors to perform operations comprising:

receiving a first data object, the first data object including:

an entity data set including a plurality of entities;

a performance history data set including a plurality of performance-related records for the plurality of entities; and one or more performance metric data sets for the plurality of entities, including active utilization data of the plurality of entities;

generating an entity data object for individual entities of the plurality of entities based on at least one of the entity data set, the performance history data set, or the one or more performance metric data sets;

identifying a subset of entities, of the plurality of entities, having a medication protocol for medical condition management that satisfies an eligibility criterion;

determining, using a machine learning model, a risk score for the individual entities of the subset of entities based on the one or more performance metric data sets included in the first data object, wherein the machine learning model is trained, based on training data, to (i) identify associations between the active utilization data and a compliance risk for the individual entities of the subset of entities and (ii) output the risk score representing the compliance risk based on the identified associations;

generating, based on the entity data object for the individual entities of the subset of entities, a compliance indicator indicating a likelihood of adherence of the respective individual entities of the subset of entities to the medication protocol;

generating, based on the entity data object and the compliance indicator, an intervention data object for the respective individual entities of the subset of entities that includes a targeted alteration to the medication protocol;

generating a utilization adjustment data object based on the entity data object, the risk score, the compliance indicator, and the intervention data object for the respective individual entities of the subset of entities, wherein the respective individual entities of the subset of entities are mapped to one of a plurality of risk groups in the utilization adjustment data object;

causing the utilization adjustment data object to be displayed on a Graphical User Interface (GUI);

in response to determining at least one individual entity of the subset of entities being mapped to a particular risk group of the plurality of risk groups, applying the targeted alteration to the medication protocol for the at least one individual entity to cause administration of an altered medication protocol to the at least one individual entity, the altered medication protocol including the targeted alteration;

monitoring a performance of the machine learning model as a new data object is received;

detecting, based on the monitoring, parameters associated with the new data object having a threshold difference from parameters associated with the training data that indicate a drift, the drift affecting the performance of the machine learning model; and in response to detecting the drift, applying a correction mechanism to optimize the performance of the machine learning model, the correction mechanism including a retraining of the machine learning model based on the parameters associated with the new data object.

14. The system of claim 13, wherein the active utilization data includes one or more active prescriptions of the medication protocol.

15. The system of claim 13, wherein determining the risk score further comprises:

applying a weight to one or more active utilizations included in the active utilization data for the individual entities of the subset of entities based on at least one of the one or more performance metric data sets, wherein a weight applied to each active utilization is determined based on a corresponding performance metric data set.

16. The system of claim 13, wherein the medication protocol for the individual entities of the subset of entities includes one or more active prescriptions associated with each respective individual entity and generating the compliance indicator includes:

receiving a complexity score for each active prescription of the one or more active prescriptions;

assigning a total complexity score, the total complexity score representing a cumulative measure of the complexity score for each active prescription of the one or more active prescriptions;

determining an adherence ratio using the total complexity score, the adherence ratio indicative of an expected proportion of days the respective individual entity is in compliance with an active prescription regimen of the medication protocol;

comparing the adherence ratio against an adherence threshold; and generating the compliance indicator, wherein a first portion of the individual entities of the subset of entities meeting or surpassing the adherence threshold are marked as compliant, and a second portion of the individual entities of the subset of entities falling below the adherence threshold are marked as non-compliant.

17. The system of claim 13, wherein identifying the subset of entities further comprises:

identifying the individual entities of the subset of entities as having at least one diagnostic indicator for a medical condition associated with the entity data object, the at least one diagnostic indicator being selected from a pre-determined plurality of diagnostic indicators associated with a chronic medical condition.

18. One or more non-transitory computer-readable media storing instructions that, when executed by one or more processors, cause the one or more processors to perform operations comprising:

receiving a first data object, the first data object including:

an entity data set including a plurality of entities;

a performance history data set including a plurality of performance-related records for the plurality of entities; and one or more performance metric data sets for the plurality of entities, including active utilization data of the plurality of entities;

generating an entity data object for individual entities of the plurality of entities based on at least one of the entity data set, the performance history data set, or the one or more performance metric data sets;

identifying, based on the entity data object for the individual entities of the plurality of entities, a subset of entities, of the plurality of entities, having a medication protocol for medical condition management that satisfies an eligibility criterion;

determining, by the one or more processors and using a machine learning model, a risk score for the individual entities of the subset of entities based on the one or more performance metric data sets included in the first data object, wherein the machine learning model is trained, based on training data, to (i) identify associations between the active utilization data and a compliance risk for the individual entities of the subset of entities and (ii) output the risk score representing the compliance risk based on the identified associations;

generating, based on the entity data object for the individual entities of the plurality of entities, a compliance indicator indicating a likelihood of adherence of the respective individual entities of the subset of entities to the medication protocol;

generating, based on the entity data object and the compliance indicator, an intervention data object for the respective individual entities of the subset of entities that includes a targeted alteration to the medication protocol;

generating a utilization adjustment data object based on the entity data object, the risk score, the compliance indicator, and the intervention data object for the respective individual entities of the subset of entities, wherein the respective individual entities of the subset of entities are mapped to one of a plurality of risk groups in the utilization adjustment data object;

causing the utilization adjustment data object to be displayed on a Graphical User Interface (GUI);

in response to determining at least one individual entity of the subset of entities being mapped to a particular risk group of the plurality of risk groups, applying the targeted alteration to the medication protocol for the at least one individual entity to cause administration of an altered medication protocol to the at least one individual entity, the altered medication protocol including the targeted alteration;

monitoring a performance of the machine learning model as a new data object is received;

detecting, based on the monitoring, parameters associated with the new data object having a threshold difference from parameters associated with the training data that indicate a drift, the drift affecting the performance of the machine learning model; and in response to detecting the drift, applying a correction mechanism to optimize the performance of the machine learning model, the correction mechanism including a retraining of the machine learning model based on the parameters associated with the new data object.

19. The one or more non-transitory computer-readable media of claim 18, wherein the medication protocol for the individual entities of the subset of entities includes one or more active prescriptions associated with each respective individual entity and generating the compliance indicator includes:

receiving a complexity score for each active prescription of the one or more active prescriptions;

assigning a total complexity score, the total complexity score representing a cumulative measure of the complexity score for each active prescription of the one or more active prescriptions;

determining an adherence ratio using the total complexity score, the adherence ratio indicative of an expected proportion of days the respective individual entity is in compliance with an active prescription regimen of the medication protocol;

comparing the adherence ratio against an adherence threshold; and generating the compliance indicator, wherein a first portion of the individual entities of the subset of entities meeting or surpassing the adherence threshold are marked as compliant, and a second portion of the individual entities of the subset of entities falling below the adherence threshold are marked as non-compliant.

\* \* \* \* \*